US011430568B2

(12) United States Patent
Hamilton et al.

(10) Patent No.: US 11,430,568 B2
(45) Date of Patent: Aug. 30, 2022

(54) METHOD AND SYSTEM FOR CONCURRENTLY MONITORING MULTIPLE OBSTETRICS PATIENTS

(71) Applicant: PERIGEN INC., Cranbury, NJ (US)

(72) Inventors: Emily Hamilton, Verdun (CA); Bruno Bendavid, Montreal (CA)

(73) Assignee: PERIGEN INC., Princeton, NJ (US)

( * ) Notice: Subject to any disclaimer, the term of this patent is extended or adjusted under 35 U.S.C. 154(b) by 197 days.

(21) Appl. No.: 16/597,408

(22) Filed: Oct. 9, 2019

(65) Prior Publication Data

US 2020/0043611 A1 Feb. 6, 2020

Related U.S. Application Data

(62) Division of application No. 15/134,712, filed on Apr. 21, 2016, now Pat. No. 10,978,202.

(51) Int. Cl.
*G16H 40/63* (2018.01)
*A61B 5/00* (2006.01)
(Continued)

(52) U.S. Cl.
CPC ........... *G16H 40/63* (2018.01); *A61B 5/0011* (2013.01); *A61B 5/4362* (2013.01); *G16H 15/00* (2018.01);
(Continued)

(58) Field of Classification Search
CPC ..................................................... G16H 40/63
See application file for complete search history.

(56) References Cited

U.S. PATENT DOCUMENTS 6,423,016 B1 7/2002 Hamilton et al.
6,907,284 B2 6/2005 Hamilton et al.
(Continued)

OTHER PUBLICATIONS

Notice of Allowance dated Dec. 21, 2020 in connection with U.S. Appl. No. 15/134,712—10 pages.
(Continued)

*Primary Examiner* — Reginald R Reyes

(57) ABSTRACT

A system, computer program product and method for facilitating concurrent monitoring of multiple obstetrics patients over a data network are proposed. Data conveying pregnancy progression information, including maternal and fetal vital sign information associated with the obstetrics patients, is received and processed to derive criticality levels for the obstetrics patients. As a first feature, notification data related to a particular obstetrics patient may be selectively transmitted to a medical expert based on different conditions including for example an associated criticality level exceeding a threshold and/or receipt of a consultation request. As a second feature, used together or separately from the first, a graphical user interface (GUI) may present a user with an ordered list of obstetrics patients dynamically adaptable based on the criticality levels. The GUI allows a user to select an obstetrics patient from the list and then adapts the GUI to present an expanded set of pregnancy progression information related to the selected obstetrics patient. Optionally, the GUI may also provide a tool allowing the user to cause a notification to be transmitted to a medical expert over the data network.

22 Claims, 13 Drawing Sheets

(51) Int. Cl.
*G16H 15/00* (2018.01)
*G16H 50/30* (2018.01)
*G16H 40/67* (2018.01)
*G16H 80/00* (2018.01)

(52) U.S. Cl.
CPC .............. *G16H 40/67* (2018.01); *G16H 50/30* (2018.01); *G16H 80/00* (2018.01)

(56) References Cited

U.S. PATENT DOCUMENTS

| | | |
|---|---|---|
| 7,113,819 B2 | 9/2006 | Hamilton et al. |
| 7,959,565 B2 | 6/2011 | Hamilton |
| 7,963,916 B2 | 6/2011 | Hamilton et al. |
| 8,636,676 B2 | 1/2014 | Hamilton |
| 8,870,793 B2 | 10/2014 | Hamilton |
| 10,134,490 B2 | 11/2018 | Hamilton |
| 10,978,202 B2 | 4/2021 | Hamilton |
| 2007/0255588 A1 | 11/2007 | Hamilton |
| 2008/0039744 A1 | 2/2008 | Hamilton |
| 2010/0268124 A1 | 10/2010 | Hamilton et al. |
| 2013/0281861 A1* | 10/2013 | Flomerfelt ............... A61B 8/02 600/483 |
| 2016/0270658 A1* | 9/2016 | Ater ..................... A61B 5/4356 |
| 2017/0308662 A1 | 10/2017 | Hamilton et al. |
| 2021/0272689 A1 | 9/2021 | Hamilton et al. |

OTHER PUBLICATIONS

Final Office Action dated Aug. 6, 2020 in connection with U.S. Appl. No. 15/134,712—6 pages.

Official Action for U.S. Appl. No. 15/134,712, dated Jan. 8, 2020 12 pages.

Clark, Steven et al.—Implementation of a conservative checklist-based protocol for oxytocin administration: maternal and newborn outcomes—American Journal of Obstetrics & Gynecology Nov. 2007—5 pages.

Clark, Steven et al.—Recognition and response to electronic fetal heart rate patterns: impact on newborn outcomes and primary cesarean delivery rate in women undergoing induction of labor—American Journal of Obstetrics & Gynecology Month 2014—6 pages.

Donna Farris—Forging Rural Health Care Links—Avera eCare, Jan.-Feb. 2015—6 pages.

Restriction Requirement issued in connection with U.S. Appl. No. 15/134,712 dated Aug. 20, 2019—6 pages.

* cited by examiner

| Site | MRN | Account N° | Name | Bed | CheckList State | CheckList Persistence | Curve % file | Last Vitals BP Oxy P RR T | CheckList | Curve |
|---|---|---|---|---|---|---|---|---|---|---|
| St. Tammany | 2376428 | 1231334 | Swan Taylor | Live - New Bed 2 | Positive | 2.5 hr | 1.5% | 210/110 99% 88 16 9.0° | Patterns | Curve |
| St. Tammany | 8268757 | 2552432 | Smith Lori | Live - New Bed 4 | Positive | 2.5 hr | 2.5% | 180/100 98% 67 18 7.1° | Patterns | Curve |
| Kenner | 5345234 | 5683566 | Brown Lucy | LDR 323 | Positive | 2.0 hr | 2.5% | 125/80 99% 78 37.8° | Patterns | Curve |
| Baptist | 5343467 | 6956856 | Penner Jane | LD 1213 | Positive | 1.4 hr | 78% | 110/90 96% 77 36.7° | Patterns | Curve |
| Baptist | 9867856 | 9656856 | Smith Loretta | LD 1233 | Positive | 1.2 hr | 62% | 135/95 95% 70 36.8° | Patterns | Curve |
| WestBank | 3535634 | 4583657 | Dilan Stacy | Room 17 | Positive | 1.2 hr | 35% | 125/80 99% 88 37° | Patterns | Curve |
| B. Rouge | 1242311 | 9656756 | Brewer Terry | LD 12 | Positive | 35 min | 78% | 110/90 96% 67 37° | Patterns | Curve |
| B. Rouge | 5432534 | 4535457 | Stolter Kelly | LD 14 | Positive | 20 min | 62% | 135/95 95% 70 37.7° | Patterns | Curve |
| B. Rouge | 8864637 | 6734575 | Abdul Dalia | LD 30 | Positive | 10 min | 35% | 125/80 99% 78 | Patterns | Curve |
| St. Anne | 5434467 | 3453734 | Love Corrine | LDR 12 | Positive | 8 min | 10% | 110/90 96% 77 | Patterns | Curve |
| St. Anne | 9648567 | 5637357 | Jones Sara | LDR 15 | Positive | 5 min | 62% | 135/95 95% 70 | Patterns | Curve |

FIG. 12

METHOD AND SYSTEM FOR CONCURRENTLY MONITORING MULTIPLE OBSTETRICS PATIENTS

CROSS-REFERENCE TO RELATED APPLICATION

The present application is a divisional application claiming de benefit of priority under 35 U.S.C. § 120 based on U.S. patent application Ser. No. 15/134,712 filed on Apr. 21, 2016 and presented pending. The contents of the above-referenced patent document are incorporated herein by reference.

FIELD OF THE INVENTION

The present invention relates generally to the field of obstetrics and, more specifically, to a method and system for the concurrent monitoring, analysing and displaying information pertaining to multiple obstetrics patients located in one or more sites of care. The invention may be particularly useful in connection with healthcare facilities handling large volumes of obstetrics patient, for example hospitals having large obstetrics wards, or facilities grouping multiple remote sites of care, for example virtual centers of expertise servicing multiple hospitals and/or birthing centers.

BACKGROUND

Birth related injuries are rare but devastating events because the consequences can lead to lifelong impairment for the baby, family and society in general. During pregnancy as well as during labor, clinical staff monitors various health characteristics of the obstetrics patients in order to obtain a qualitative assessment of the mother's and the fetus's well-being.

Access to highly qualified obstetrics personnel is however a challenge due in part to the scarcity of such personnel. It is not unusual during certain time periods for a single physician to oversee the entire obstetrics ward of a hospital in a large urban area. The problem is often even more acute in lower volume areas (e.g., remote regions and/or smaller towns), some of which may not have highly qualified obstetrics personnel on site at all and may need to rely on a physician servicing multiple locations across a relatively large geographical area.

While different tools have been developed for allowing clinical staff to remotely monitor multiple patients, the capabilities of such tools are limited insofar as to provide suitable functionality in the context of obstetrics patients, and in particular in connection with labour monitoring and assistance during pregnancy and childbirth.

In the context of the above, there is a need in the industry to provide methods and systems suitable for providing labour monitoring support and assistance during pregnancy and childbirth that alleviate at least in part problems associated with the existing methods and systems.

SUMMARY

In accordance with a first aspect, a computer program product is presented comprising one or more tangible non-transitory computer readable storage media storing computer executable instructions, for concurrently monitoring a set of obstetrics patients over a data network, the set of obstetrics patients including two or more obstetrics patients. The computer executable instructions, when executed, cause a programmable system including at least one programmable processor to perform operations, the operations comprising:

receiving data over the data network from one or more computing devices interconnected with the programmable system over the data network, the received data conveying pregnancy progression information associated with respective obstetrics patients in the set of obstetrics patients being monitored, the pregnancy progression information including at least maternal physiological information and fetal vital sign information associated with the respective obstetrics patients in the set of obstetrics patients being monitored, at the programmable system, processing the data conveying the pregnancy progression information to derive respective criticality levels for the obstetrics patients in the set of obstetrics patients being monitored, the respective criticality levels being derived at least in part by processing the maternal physiological information and the fetal vital sign information;

selectively transmitting electronic notification data over the data network in connection with a particular obstetrics patient at least in part by processing a criticality level associated with the particular obstetrics patient and a threshold criticality level, the electronic notification data being transmitted to a computing device associated with a particular medical expert.

In some specific practical implementations, the computing device associated with the particular medical expert may include a smartphone, a tablet, a general purpose computer and/or any other suitable computing device and the electronic notification data may convey an e-mail message, an SMS message and/or or any other suitable electronic message.

In some specific practical implementations, the electronic notification data is configured for causing a graphical user interface (GUI) to be displayed on a display screen of the computing device associated with the particular medical expert, the GUI including pregnancy progression information elements associated with the particular obstetrics patient. The pregnancy progression information elements presented on the GUI may form an initial set of pregnancy progression information elements associated with the particular obstetrics patient. In some implementations, the GUI caused to be displayed by the electronic notification data may provide a user operable control component to enable the medical expert to request additional information associated with the particular obstetrics patient. The user operable control component may include any suitable input mechanism for enabling the medical expert to convey a command including (without being limited to) a hyperlink, a touch sensitive area on the display and a voice control input.

According to some specific specific implementations, the operations performed at the programmable system may further comprise receiving from the computing device associated with the particular medical expert information conveying a request for additional information associated with the particular obstetrics patient and transmitting data over the data network to the computing device associated with the medical expert to adapt the GUI to present the medical expert with an expanded set of pregnancy progression information elements associated with the particular obstetrics patient.

Jointly, or independently with the specific practical implementations described above, the GUI caused to be displayed by the electronic notification data may provide the medical expert with a(nother) user operable control component to enable the medical expert to establish a communication with a computing device located in proximity to the particular obstetrics patient. For example, the communication established with the computing device associated with the particular obstetrics patient may include one of a telephone call, a video call, an e-mail, an SMS message, an audio alarm trigger and/or a visual alarm trigger. Such communication may allow the medical expert, who may be remotely located, to interact with the particular obstetrics patient herself and/or with a person at the bedside of the obstetrics patient, which may include a friend/spouse and/or a member of the clinical staff. The type of communication established may vary depending on the particular implementation and/or may be selected by the medical expert through the GUI by providing an input object conveying suitable selectable options on the GUI. In implementations in which the GUI provides the medical expert with selectable options for the type of communication, the types of the selectable options may in some cases be dynamically adaptable so as to present the medical expert with options customized to particular circumstances associated with the patient. For example, in a case where the electronic notification data was sent in part as a result of a consultation request, the selectable options may include a telephone call and a video call but exclude an audio alarm trigger and/or a visual alarm trigger to reduce the likelihood the medical expert may trigger alarms unnecessarily. As another example, in a case where the electronic notification data was sent in part as a result of a criticality level exceeding a threshold, the selectable options may include an audio alarm trigger and/or a visual alarm trigger in addition to other options.

Jointly with, or independently from, the specific practical implementations described above, the GUI caused to be displayed by the electronic notification data may provide the medical expert with a(nother) user operable control component to enable the medical expert to trigger transmittal of further notification data associated with the particular obstetrics patient over the data network. Optionally, the GUI may also provide the medical expert with one or more user operable control components to allow the medical expert to provide specific requests for medical care in connection with the particular obstetrics patient so that such specific requests are included as part of further notification data. Such one or more user operable control components may be in the form of user editable text boxes, menus including sets of selectable medical care options and/or any other suitable mechanism for allowable the medical expert to provide such information through the GUI. The further electronic notification data may be transmitted to a computing device associated with a clinical staff member located in proximity to the particular obstetrics patient.

In practical implementations, such notification data may allow the medical expert, who may be remotely located, to refer the particular obstetrics patient to a member of the clinical staff located near the obstetrics patient, for example in the same hospital and/or by the patient's bedside. In some specific practical implementations, the further electronic notification data may be in a form similar to the electronic notification data that was sent by the programmable system and may be configured for causing a graphical user interface (GUI), analogous to that displayed on the (initial) device associated with the medical expert, to be displayed on a display screen of a computing device associated with the member of the clinical staff located near the obstetrics patient. Optionally, the GUI displayed to the member of the clinical staff located near the obstetrics patient may also convey the specific requests for medical care provided by the medical expert in connection with the particular obstetrics patient.

According to some specific implementations, the operations performed at the programmable system may comprise receiving data over the data network from a particular computing device interconnected with the programmable system over the data network, the received data conveying a consultation request associated with the particular obstetrics patient. The consultation request may originate from a computing device located in proximity to the particular obstetrics patient or from another device. In some specific implementations, selectively transmitting electronic notification data over the data network in connection with the particular obstetrics patient may performed at least in part by processing the criticality level associated with the particular obstetrics patient and the threshold criticality level and/or processing the received consultation request associated with the particular obstetrics patient.

According to some specific implementations, different threshold criticality levels may be contemplated, where exceeding each threshold may trigger different types of electronic notifications and/or may cause electronic notifications to be transmitted to different medical experts. For example, the threshold criticality level may be a first threshold criticality level and the electronic notification data generated as a result of exceed the first threshold criticality level may convey a notification of a first type. The operations performed at the programmable system may further comprise selectively transmitting electronic notification data conveying a notification of a second type over the data network in connection with the particular obstetrics patient following the criticality level associated with the particular obstetrics patient exceeding a second threshold criticality level distinct from the first threshold criticality level. The electronic notification data conveying the notification of the second type may be transmitted to the same medical expert as the electronic notification of the first type or, alternatively, may be transmitted to a different medical expert, for example a medical expert having more experience in trauma for example and/or a medical expert that may be located in closer proximity to the particular obstetrics patient than the original medical expert.

In accordance with a second aspect, a method is presented for concurrently monitoring a set of obstetrics patients over a data network, the set of obstetrics patients including two or more obstetrics patients. The method is implemented by a programmable system including one or more processor and comprises:

receiving data over the data network from one or more computing devices interconnected with the programmable system over the data network, the received data conveying pregnancy progression information associated with respective obstetrics patients in the set of obstetrics patients being monitored, the pregnancy progression information including at least maternal physiological information and fetal vital sign information associated with the respective obstetrics patients in the set of obstetrics patients being monitored, processing the data conveying the pregnancy progression information to derive respective criticality levels for the obstetrics patients in the set of obstetrics patients being monitored, the respective criticality levels being derived at least in part by processing the maternal physiological information and the fetal vital sign information;

selectively transmitting electronic notification data over the data network in connection with a particular obstetrics patient at least in part by processing a criticality level associated with the particular obstetrics patient and a threshold criticality level, the electronic notification data being transmitted to a computing device associated with a particular medical expert.

In accordance with a third aspect, apparatus is presented for use in concurrently monitoring a set of obstetrics patients over a data network, the set of obstetrics patients including two or more obstetrics patients. The apparatus comprises an input for receiving data over the data network from one or more computing devices, the received data conveying pregnancy progression information associated with respective obstetrics patients in the set of obstetrics patients being monitored, the pregnancy progression information including at least maternal physiological information and fetal vital sign information associated with the respective obstetrics patients in the set of obstetrics patients being monitored. The apparatus also comprises a processing module in communication with the input. The processing module is programmed for processing the data conveying the pregnancy progression information to derive respective criticality levels for the obstetrics patients in the set of obstetrics patients being monitored, the respective criticality levels being derived at least in part by processing the maternal physiological information and the fetal vital sign information. The processing module is also programmed for processing the derived criticality levels to identify one or more particular obstetrics patients, wherein said processing includes comparing the derived criticality levels to a threshold criticality level. The processing module is also programmed for causing electronic notifications to be selectively transmitted over the data network in connection with the one or more particular obstetrics patients, at least some of the electronic notifications being transmitted to computing devices associated with particular medical experts.

In accordance with a fourth aspect, a system is presented for use in concurrently monitoring a set of obstetrics patients over a data network, the set of obstetrics patients including two or more obstetrics patients. The system comprises one or more devices configured for obtaining pregnancy progression information associated with respective obstetrics patients in the set of obstetrics patients being monitored. The system also comprises a clinical monitoring module interconnected with the one or more devices over the data network. The clinical monitoring module is configured for receiving data from the one or more devices, said data conveying the pregnancy progression information associated with the respective obstetrics patients in the set of obstetrics patients being monitored, the pregnancy progression information including at least maternal physiological information and fetal vital sign information associated with the respective obstetrics patients in the set of obstetrics patients being monitored. The clinical monitoring module is also configured for processing the data conveying the pregnancy progression information to derive respective criticality levels for the obstetrics patients in the set of obstetrics patients being monitored, the respective criticality levels being derived at least in part by processing the maternal physiological information and the fetal vital sign information. The clinical monitoring module is also configured for selectively transmitting electronic notification data over the data network in connection with a particular obstetrics patient following a criticality level associated with the particular obstetrics patient exceeding a threshold criticality level, the electronic notification data being transmitted to a computing device associated with a particular medical expert.

According to some specific implementations, the electronic notification data is configured for causing a graphical user interface (GUI) to be displayed on a display screen of the computing device associated with the particular medical expert, the GUI including pregnancy progression information elements associated with the particular obstetrics patient. The GUI may provide the medical expert with one or more user operable control components to enable the medical expert to perform different functions such as, for example, requesting additional information associated with the particular obstetrics patient and/or establishing a communication with a computing device located in proximity to the particular obstetrics patient. In some practical implementations, the communication established with the computing device located in proximity to the particular obstetrics patient may be a telephone call, a video call, an e-mail, an SMS message, an audio alarm trigger, a visual alarm trigger or any other suitable form of communication.

In accordance with a fifth aspect, a method is presented for monitoring a set of obstetrics patients over a data network, the set of obstetrics patients including two or more obstetrics patients. The method is implemented by a computing device including one or more processor and a display screen and comprises receiving electronic notification data associated with a particular obstetrics patient from a clinical monitoring module, the electronic notification data being configured for causing a graphical user interface (GUI) to be displayed on the display screen of the computing device, the GUI including pregnancy progression information elements associated with the particular obstetrics patient, wherein the pregnancy progression information elements form an initial set of pregnancy progression information elements associated with the particular obstetrics patient. The GUI provides a user of the computer device with a user operable control component to enable the user to request additional information associated with the particular obstetrics patient. The method further comprises, in response to actuation of the user operable control component by the user of the computing device:
  causing a signal conveying a request for additional information to be transmitted from the computing device to the clinical monitoring module;
  receiving data from the clinical monitoring module over the data network, the data being configured to adapt the GUI displayed on the displayed device to present the user with an expanded set of pregnancy progression information elements associated with the particular obstetrics patient.

According to some specific implementations, the user operable control component may be one of multiple user operable control component. In specific practical implementations, the GUI may provide the medical expert with another user operable control component to enable the user to establish a communication with a computing device located in proximity to the particular obstetrics patient. In some practical implementations, the communication established with the computing device located in proximity to the particular obstetrics patient may be a telephone call, a video call, an e-mail, an SMS message, an audio alarm trigger, a visual alarm trigger or any other suitable form of communication.

In other specific practical implementations, the GUI may provide the medical expert with another user operable control component to enable the user to trigger transmittal of further notification data associated with the particular obstetrics patient over the data network, the further electronic notification data being transmitted to a computing device located in proximity to the particular obstetrics patient. Such further electronic notification data may convey an e-mail, an SMS message, an audio alarm trigger, a visual alarm trigger and/or any other suitable type of notification. In a specific practical implementation, the further notification data may convey one or more specific requests for medical care in connection with the particular obstetrics patient. Optionally, the GUI presented may provide the medical expert with one or more user operable control components to allow the medical expert to provide specific requests for medical care in connection with the particular obstetrics patient so that such specific requests are included as part of further notification data. Such one or more user operable control components may be in the form of user editable text boxes, menus including a set of selectable medical care options and/or any other suitable mechanism for allowable the medical expert to provide such information through the GUI. The further electronic notification data may be transmitted to a computing device associated with a clinical staff member located in proximity to the particular obstetrics patient.

In accordance with yet another broad aspect, a computer program product is presented comprising one or more tangible non-transitory computer readable storage media storing computer executable instructions, for allowing a user to concurrently monitor a set of obstetrics patients over a data network, the set of obstetrics patients including two or more obstetrics patients. The computer executable instructions, when executed, cause a programmable system including at least one programmable processor to perform operations, the operations comprising:
  receiving data over the data network from one or more computing devices interconnected with the programmable system over the data network, the received data conveying pregnancy progression information associated with respective obstetrics patients in the set of obstetrics patients being monitored, the pregnancy progression information including at least maternal physiological information and fetal vital sign information obtained over time and being associated with the respective obstetrics patients in the set of obstetrics patients being monitored;
  at the programmable system, processing the data conveying the pregnancy progression information to derive respective criticality levels for the obstetrics patients in the set of obstetrics patients being monitored, the respective criticality levels being derived at least in part by processing the maternal physiological information and the fetal vital sign information;
  transmitting data to a computing device associated with the user to adapt a graphical user interface (GUI) to provide the user with an input object presenting the user with:
    a. an ordered list including selectable entries associated with one or more obstetrics patients from the set of obstetrics patients being monitored, the ordered list being derived at least in part by processing the derived respective criticality levels for the obstetrics patients in the set of obstetrics patients being monitored, the selectable entries in said ordered list being arranged in order based on the derived respective criticality levels;
    b. said input object being configured to accept a user input specifying a particular obstetrics patient among the one or more obstetrics patients associated with the selectable entries presented to the user;
  receiving from the computing device associated with the user information input by the user conveying a selection by the user of the particular obstetrics patient at the input object;
  transmitting data to the computing device associated with the user to adapt the GUI at the computing device to present the user with an expanded set of pregnancy progression information element associated with the particular obstetrics patient.

In some specific practical implementations, the GUI may be adapted to present the user with the expanded set of pregnancy progression information element associated with the particular obstetrics patient jointly with the ordered list including selectable entries associated with one or more obstetrics patients from the set of obstetrics patients being monitored. Advantageously, this may allow the user to visually examine expanded information pertaining to a particular patient while maintaining an overview of the overall set of obstetrics patients being monitored and their relative levels of criticality through the ordered list.

In some specific practical implementations, the GUI may be configured to assign visual identifiers to the selectable entries in the ordered list in accordance with visual identifier code, a specific visual identifier in the visual identifier code being assigned to a specific entry in the ordered list associated with the particular obstetrics patient at least in part based on a specific criticality level derived in connection with the particular obstetrics patient. In practical implementations, different types of visual identifier codes may be used including, without being limited to, a color code, changes in font sizes, "blinking" displays or any other manner that may assist a user in visually distinguishing between the selectable entries in the ordered list.

In specific implementations, the operations may further comprise processing the data conveying the pregnancy progression information to adjust over time the derived respective criticality levels for the obstetrics patients in the set of obstetrics patients being monitored and transmitting data to the computing device associated with the user to cause the graphical user interface (GUI) to be dynamically adapted over time to present the user with versions of the ordered list adjusted over time, the adjusted versions of the ordered list being derived at least in part by processing the criticality levels for the obstetrics patients adjusted over time.

In some specific practical implementations, the GUI may provide the user with a user operable control component to enable the user to cause electronic notification data to be transmitted over the data network in connection with the particular obstetrics patient specified by the user input, the electronic notification data being transmitted to a computing device associated with a particular medical expert. The electronic notification data transmitted to the computing device associated with the particular medical expert may be configured for causing a graphical user interface (GUI) to be displayed on a display screen of the computing device associated with the particular medical expert, the GUI including pregnancy progression information elements associated with the particular obstetrics patient.

In accordance with yet another aspect, a method is presented for allowing a user to concurrently monitor a set of obstetrics patients over a data network, the set of obstetrics patients including two or more obstetrics patients. The method is implemented by a programmable system including at least one programmable processor and comprises receiving data over the data network from one or more computing devices interconnected with the programmable system over the data network, the received data conveying pregnancy progression information associated with respective obstetrics patients in the set of obstetrics patients being monitored, the pregnancy progression information including at least maternal physiological information and fetal vital sign information obtained over time and being associated with the respective obstetrics patients in the set of obstetrics patients being monitored. The method also comprises, using the programmable system to process the data conveying the pregnancy progression information to derive respective criticality levels for the obstetrics patients in the set of obstetrics patients being monitored, the respective criticality levels being derived at least in part by processing the maternal physiological information and the fetal vital sign information. The method also comprises transmitting data to a computing device associated with the user to adapt a graphical user interface (GUI) to provide the user with an input object presenting the user with an ordered list including selectable entries associated with one or more obstetrics patients from the set of obstetrics patients being monitored, the ordered list being derived at least in part by processing the derived respective criticality levels for the obstetrics patients in the set of obstetrics patients being monitored, the selectable entries in said ordered list being arranged in order based on the derived respective criticality levels. The input object provided at the GUI is configured to accept a user input specifying a particular obstetrics patient among the one or more obstetrics patients associated with the selectable entries presented to the user. The method also comprises receiving from the computing device associated with the user information input by the user conveying a selection by the user of the particular obstetrics patient at the input object. The method also comprises processing the selection by the user to derive an expanded set of pregnancy progression information associated with the particular obstetrics patient and transmitting data to the computing device associated with the user to adapt the GUI at the computing device to present the user with the expanded set of pregnancy progression information element.

In accordance with yet another aspect, a system is presented for concurrently monitoring a set of obstetrics patients over a data network, the set of obstetrics patients including two or more obstetrics patients. The system comprises one or more devices configured for obtaining pregnancy progression information associated with respective obstetrics patients in the set of obstetrics patients being monitored. The system also comprises a display device associated with the user and a clinical monitoring module interconnected with the one or more devices and with the display device. The clinical monitoring module is configured for:

receiving data from the one or more devices, said data conveying the pregnancy progression information associated with the respective obstetrics patients in the set of obstetrics patients being monitored, the pregnancy progression information including at least maternal physiological information and fetal vital sign information associated with the respective obstetrics patients in the set of obstetrics patients being monitored;

processing the data conveying the pregnancy progression information to derive respective criticality levels for the obstetrics patients in the set of obstetrics patients being monitored, the respective criticality levels being derived at least in part by processing the maternal physiological information and the fetal vital sign information;

causing a graphical user interface (GUI) to be displayed on the display device user, the GUI providing the user with an input object presenting the user with:

an ordered list including selectable entries associated with one or more obstetrics patients from the set of obstetrics patients being monitored, the ordered list being derived at least in part by processing the derived respective criticality levels for the obstetrics patients in the set of obstetrics patients being monitored, the selectable entries in said ordered list being arranged in order based on the derived respective criticality levels;

said input object being configured to accept a user input specifying a particular obstetrics patient among the one or more obstetrics patients associated with the selectable entries presented to the user;

receiving user information input by the user conveying a selection by the user of the particular obstetrics patient at the input object;

processing the selection by the user to derive an expanded set of pregnancy progression information associated with the particular obstetrics patient and adapt the GUI displayed on the display device to present the user with the expanded set of pregnancy progression information element.

Some practical implementations of the systems and principles described in the present document may allow healthcare facilities, healthcare networks, healthcare practitioners, technical support personnel, and/or other users to improve obstetric patient care and provide enhanced telepresence services to obstetric patients while reducing the costs associated with telepresence consultations to obstetric patients and/or otherwise improve existing technologies and systems for the concurrent monitoring, analysing and displaying of information pertaining to multiple obstetrics patients. Suitable networks for use with the present system include any of a wide variety of physical infrastructures, protocols, connections, and encryption algorithms. According to various embodiments, suitable networking practices may be implemented in order to comply with accepted healthcare standards and/or government regulations, such as for example practices for ensuring confidentiality of patient information.

All features of embodiments which are described in this disclosure and are not mutually exclusive can be combined with one another. Elements of one embodiment can be utilized in the other embodiments without further mention. Other aspects and features of the present invention will become apparent to those ordinarily skilled in the art upon review of the following description of specific embodiments in conjunction with the accompanying Figures.

BRIEF DESCRIPTION OF DRAWINGS

A detailed description of specific embodiments is provided herein below with reference to the accompanying drawings in which:

FIG. 12 shows another specific example of implementation of a GUI presenting a user with an ordered list including selectable entries associated with one or more obstetrics patients being monitored, wherein the GUI may be caused to be displayed on a display device by the clinical monitoring module 150 of the type shown in FIGS. 1 and 3 in accordance with another non-limiting example of implementation.

Figure 1:
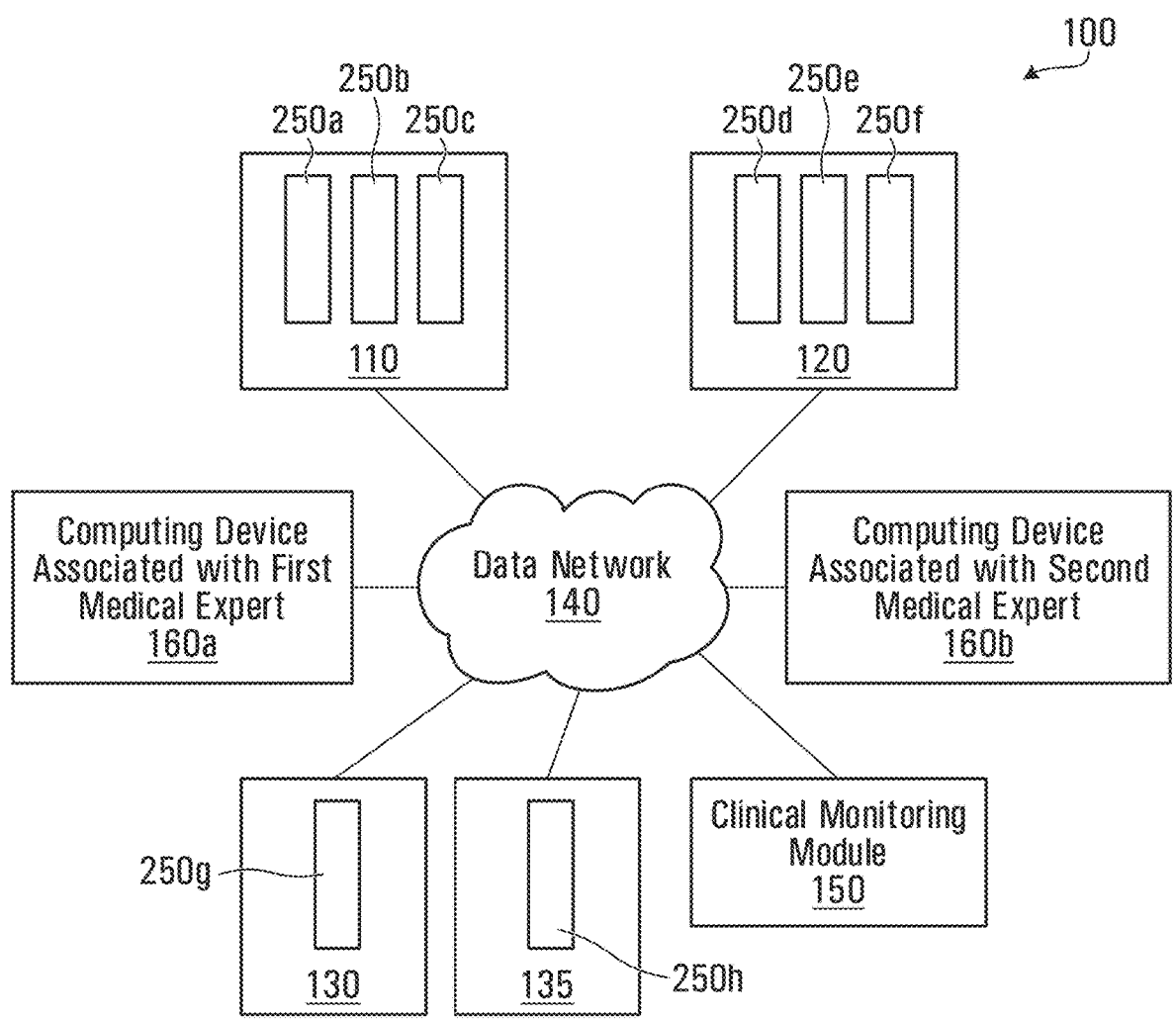
FIG. 1 is a block diagram showing a system 100, including a clinical monitoring module 150, for concurrently monitoring a set of obstetrics patient stations over a data network 140 in accordance with a non-limiting example of implementation of the invention.

In the drawings, embodiments are illustrated by way of example. It is to be expressly understood that the description and drawings are only for the purpose of illustrating certain embodiments and are an aid for understanding. They are not intended to be a definition of the limits of the invention.

DETAILED DESCRIPTION

The present invention aims to improve the concurrent monitoring, analysing and displaying of information pertaining to multiple obstetrics patients located in one or more sites of care, for example in hospitals having large obstetrics wards, or facilities grouping multiple remote sites of care, for example virtual centers of expertise servicing multiple hospitals and/or birthing centers and/or individual homes. It is to be understood that for the purpose of this specification, the expression "medical expert" is used broadly to encompass medical staff involved in obstetrics care, such as a nurse, a medical doctor, midwife or the like.

It is also to be appreciated that tools incorporating features described in the present document may be suitable for use at different stages during pregnancy, including prior to and during and labour/childbirth. It is therefore to be appreciated that pregnancy progression information is therefore meant to capture information that may be used during active labour monitoring (e.g. labour progression information) as well as monitoring pregnancy prior to labour (e.g. pre-labour information).

The system proposed according to a specific example monitors pregnancy progression measurements and data derived using various tools and may provide alerts/notifications when certain conditions are met by specific individual obstetrics patients. The tools may include, for example, various tools developed by Perigen Inc. such as for example PeriCALM®Tracings™, PeriCALM®Patterns™, PeriCALM® Curve™ and PeriCALM® ShoulderScreen™ amongst others.

With reference to FIG. 1, there is shown a system 100 for use in concurrently monitoring a set of obstetrics patients over a data network 140 in accordance with a specific example of implementation. As shown, the system 100 is comprised of a plurality of devices interconnected over a data network 140. The plurality of devices may include a plurality of obstetrics patient stations $250_{a\ldots h}$ located in one or more sites of care 110, 120, 130 and 135, a plurality of computing devices $160_{a,b}$ associated with respective medical experts and a clinical monitoring module 150.

Generally, the obstetrics patient stations $250_{a\ldots h}$ are configured to monitor various parameters pertaining to pregnancy progression, including maternal physiological information and fetal vital sign information, for respective obstetrics patients. In accordance with the embodiment depicted, the obstetrics patient stations $250_{a\ldots h}$ are in communication with the clinical monitoring module 150 and/or with one or more of the computing devices $160_{a,b}$ associated with respective medical experts over the data network 140.

The computing devices $160_{a,b}$ associated with respective medical experts may establish communications with the clinical monitoring module 150 and/or with one or more of the obstetrics patient stations $250_{a\ldots h}$ over the data network 140. While two computing devices $160_{a,b}$ have been depicted in FIG. 1, it is to be appreciated that the system 100 may include any number of such devices. As will be described later on in the present document, in the context of the system 100 depicted in FIG. 1, a computing device $160_a$ or $160_b$ may be used to receive electronic notifications originating from the clinical monitoring module 150; and/or to establish communications with specific obstetrics patient stations $250_{a\ldots h}$ and/or to establish communications with other computing devices $160_a$ or $160_b$.

The clinical monitoring module 150 may be configured for receiving, over the data network 140, data conveying pregnancy progression information originating from the obstetrics patient stations $250_{a\ldots h}$ and for processing such data to derive useful information in connection with the monitoring of pregnancy progression information associated with respective obstetrics patients.

In some implementations, the clinical monitoring module 150 may also be configured to transmit data to the obstetrics patient stations $250_{a\ldots h}$ and/or to the computing devices $160_{a,b}$ associated with respective medical experts over the data network 140. A description of the functionality of the clinical monitoring module 150 will be described later on in greater detail in the present document.

In practical implementations, the system 100 of FIG. 1 may be of a distributed nature where the obstetrics patient stations $250_{a\ldots h}$, the clinical monitoring module 150 and computing devices $160_{a,b}$ may be in different locations and be interconnected through data network 140.

In practical implementations, the data network 140 may be any suitable data network including but not limited to public network (e.g., the Internet), a private network (e.g., a LAN or WAN), a wired network (e.g., Ethernet network), a wireless network (e.g., an 802.11 network or a Wi-Fi network), a cellular network (e.g., a Long Term Evolution (LTE) network), routers, hubs, switches, server computers, and/or any combinations thereof.

Examples of implementation of the obstetrics patient stations $250_{a\ldots h}$, of the computing devices $160_{a,b}$ associated with respective medical experts, and of the clinical monitoring module 150 suitable for use with the system 100 will now be described in greater details. Example of processes that may be implemented by such devices will also be described.

Obstetrics Patient Stations $250_{a\ldots h}$

In accordance with some specific practical implementations, each one of the obstetrics patient stations $250_{a\ldots h}$ may include one or more devices for gathering pregnancy progression information in connection with a respective particular obstetrics patient or with a subgroup of obstetrics patients within a remote site of care.

In certain embodiments, the obstetrics patient stations $250_{a\ldots h}$ can each be directly connected to the data network 140 via any suitable hardware/software components, or can be connected with each other via a private network (e.g. a Local Area Network (LAN)), which in turn, can be connected to the data network 140 (e.g. which may be a Wide Area Network (WAN) and/or a public network such as the Internet). The communication link between the obstetrics patient stations $250_{a\ldots h}$ and the data network 140 can be metallic conductors, optical fibers or wireless. The specific nature of the hardware/software used to establish a communication between the obstetrics patient stations $250_{a\ldots h}$ and the data network 140 may vary between implementations and is not critical to the present invention and will therefore not be described in further detail here.

Figure 2:
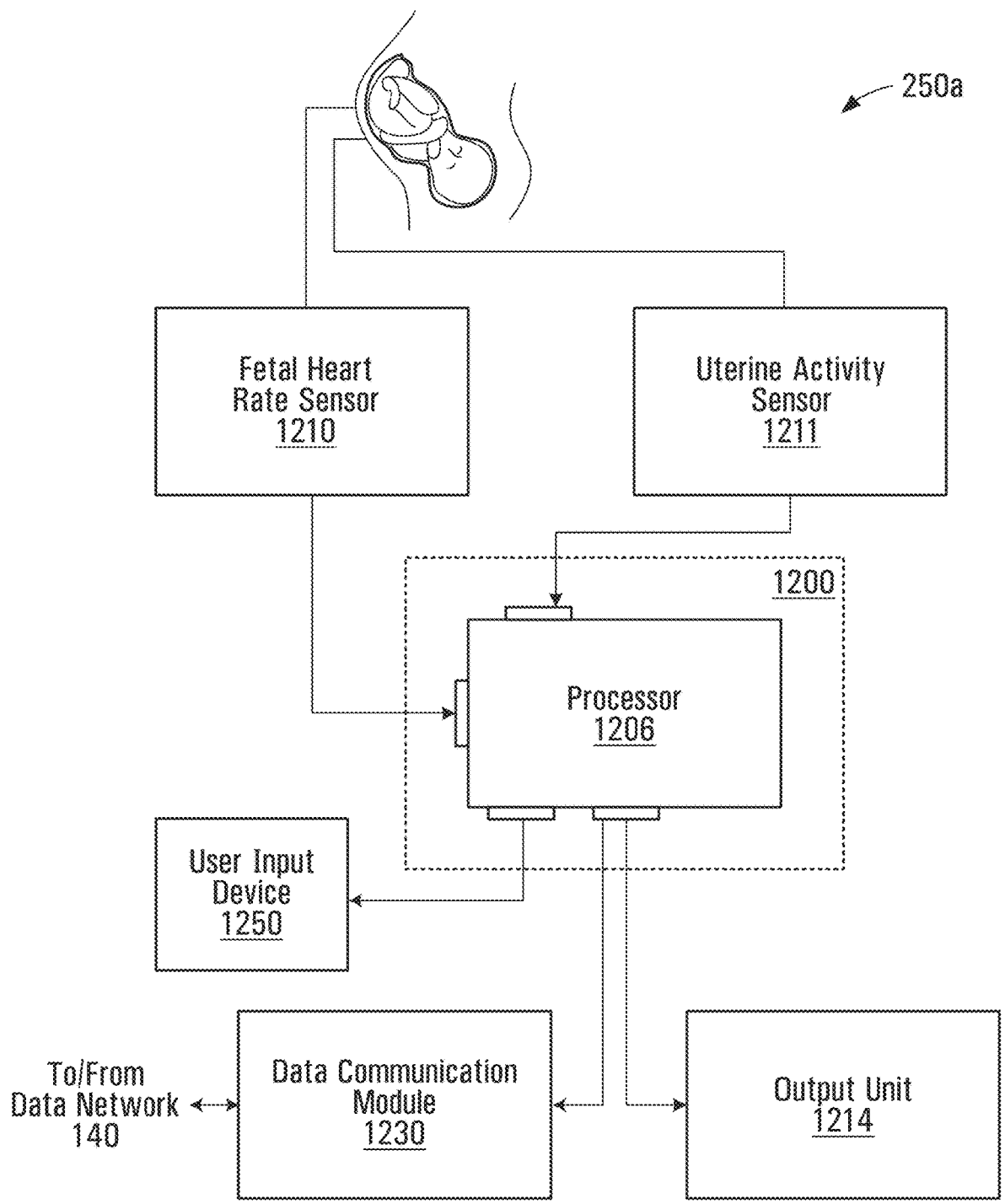
FIG. 2 is a block diagram showing one (1) obstetrics patient station $250_a$, for use in connection with the system 100 of FIG. 1, including devices for gathering labouring progression information in connection with a particular obstetrics patient in accordance with a non-limiting example of implementation.

With reference to FIG. 2, there is shown an example of a configuration of one (1) of the obstetrics patient stations $250_{a\ldots h}$ of the system 100 depicted in FIG. 1, namely obstetrics patient station $250_a$, which is located in a specific site of care 110 along with obstetrics patient station $250_b$ and obstetrics patient station $250_c$.

It is to be appreciated that the other patient stations $250_{b\ldots h}$ of the system 100 may have similar or different configurations from what is shown in FIG. 2 and may implement similar or different functions from those described herein below with reference to obstetrics patient station $250_a$. Therefore the present description should be considered as illustrating one amongst different possible implementations for patient stations $250_{a\ldots h}$.

As depicted, the obstetrics patient station $250_a$ includes a fetal heart rate sensor 1210, a uterine activity sensor 1211, an apparatus 1200 implementing some tools for monitoring a mother and baby in-utero during labour, an output unit 1214 for conveying information provided by the apparatus 1200 and a data communication module 1230 for allowing the apparatus 1200 to communicate with other devices over data network 140 (shown in FIG. 1).

The fetal heart rate sensor 1210 is for detecting a fetal heart rate of a baby in-utero, also referred to as a fetus in the womb. Fetal heart rate sensors are well known in the art to which this invention pertains and as such will not be described further here. The uterine activity sensor 1211 is for monitoring uterine activity (i.e., a tocodynamometer—also referred to as "TOCO") and is configured to sample uterine pressure of the mother during labour. Sensors for monitoring uterine activity are well known in the art to which this invention pertains and as such will not be described further here.

Optionally, the obstetrics patient station $250_a$ may further include a user input device 1250 for receiving data from a user of the system. The data may convey commands directed to controlling various features of the tools implemented by apparatus 1200 and, optionally, may also convey various measurements taken and associated with the obstetrics patients, such as for example (but not limited to) cervical dilation measures and levels of fetal descent. The type of data received through such a user input device may vary between different practical implementations. Alternatively, or in addition, the user input device 1250 may allow a user to issue a request for a medical consultation (also referred to as a consultation result in the present document) over the data network 140 as will be described later on. The user input device 1250 may include any one or a combination of the following: keyboard, pointing device, touch sensitive surface, actuator/selection switches or speech recognition unit.

Optionally still, the obstetrics patient station $250_a$ may further include other sensors (not shown) for obtaining maternal physiological information and fetal vital sign information useful in measuring pregnancy progress and the baby's tolerance to labor. Such sensors may include, for example but not limited to, a sensor for measuring the maternal oxygen saturation and a sensor for measuring maternal blood pressure. The specific manner in which data generated using these other sensors (or data obtained through a user input device) may be used in assessing pregnancy progression and the baby's tolerance to labor is beyond the scope of the present application and thus will not be described further here. The person skilled in the art will however appreciate that the methods and approaches presented in the present application may be used alone or in combination with other methods and approaches to generate information for assisting clinical staff in assessing pregnancy progression and the baby's tolerance to labor.

The output unit 1214 is in communication with the apparatus 1200 and receives signals causing the output unit 1214 to convey pregnancy progression information. The output unit 1214 may be located by the bedside of the obstetrics patient or, alternatively, may be located at a nurse's station in the vicinity of the patient. The output unit 1214 may be in the form of a display screen, a printer or any other suitable device for conveying to a physician or other health care professional information conveying pregnancy progression and fetal well-being. In a non-limiting implementation, the output unit 1214 includes one or more display monitors to display information in a visual format based on data and/or signals provided by the apparatus 1200. The information displayed may be derived by the apparatus 1200 or may be derived by another device (e.g. the clinical monitoring module 150 shown in FIG. 1 or another device) and communicated to the apparatus 1200 over the data network 140 via the data communication module 1230. In non-limiting examples, the display monitor may be a computer screen associated with a computer workstation, the display screen of a computer tablet or the display screen of smart-phone. In specific practical implementations, the output unit 1214 may be located in proximity to the obstetrics patient, such as for example by the patient's bedside and/or at a nurse's station in an obstetrics ward in which the patient is located.

Figure 4:
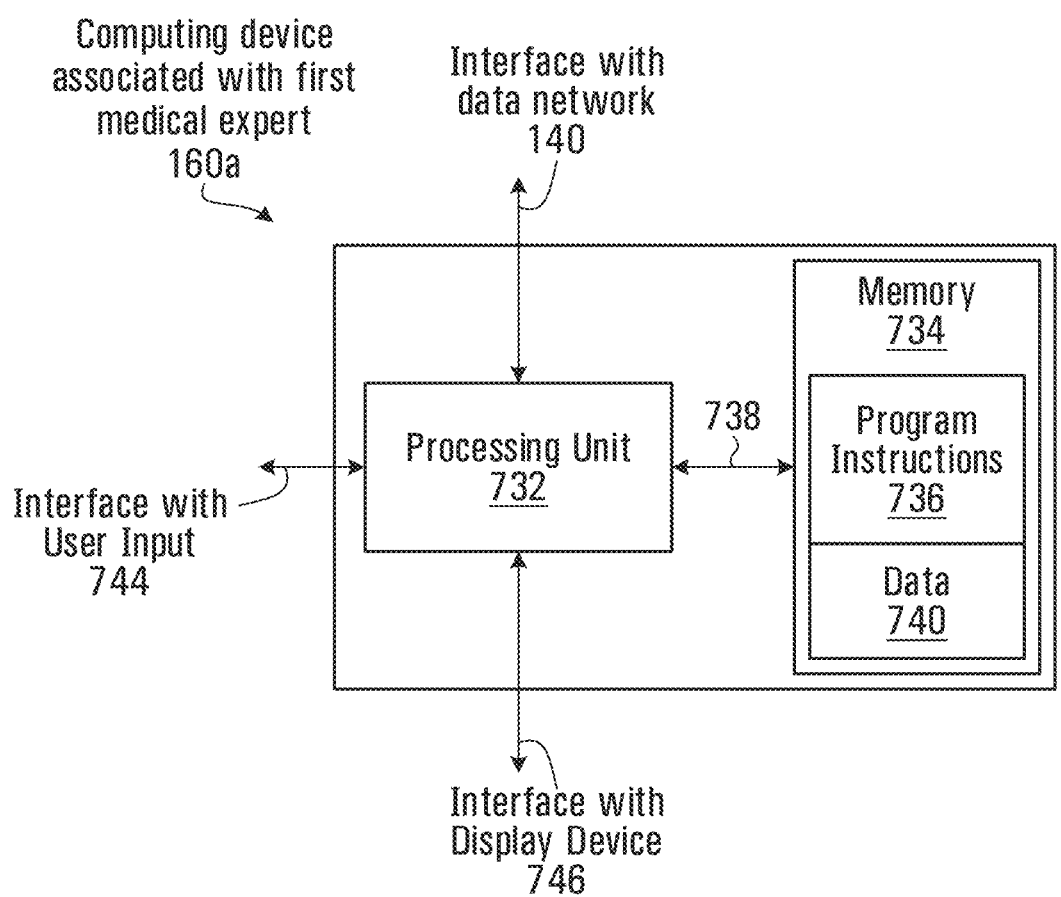
FIG. 4 is a block diagram of a device that may be used by a medical expert in connection with the system of FIG. 1 in accordance with a non-limiting example of implementation.
Figure 11:
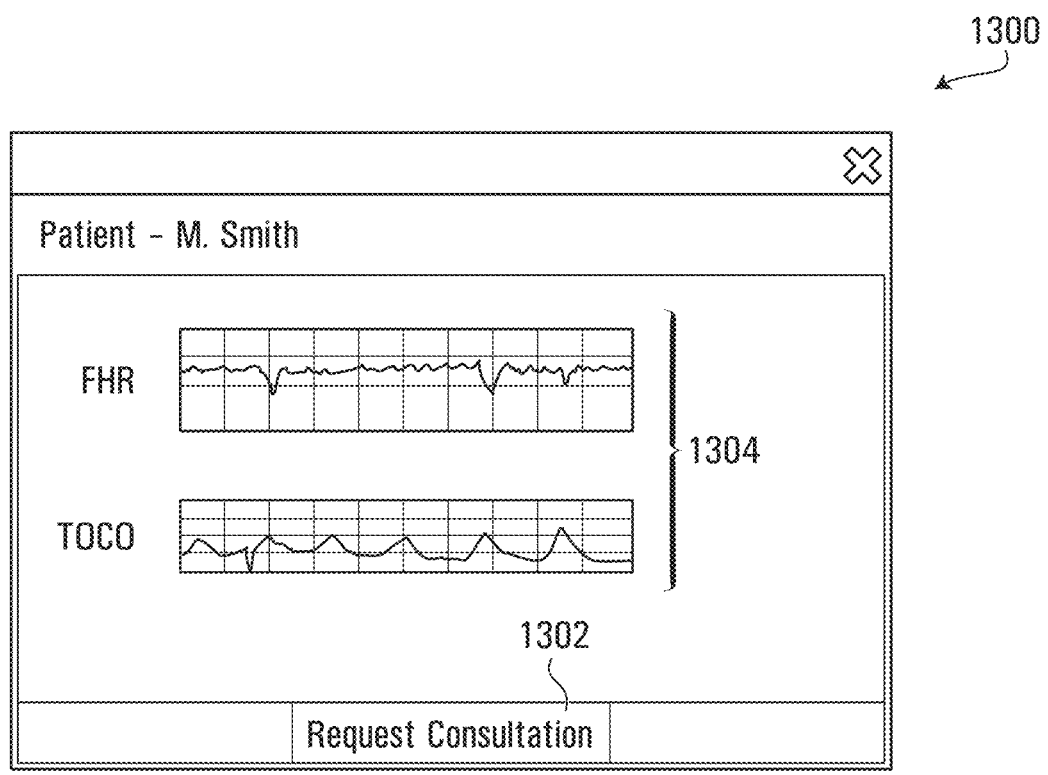
FIG. 11 shows a graphical user interface (GUI) that may be displayed on an output unit of an obstetrics patient station of the type shown in FIG. 2 in accordance with a non-limiting example of implementation.

FIG. 11 shows a graphical user interface (GUI) 1300 that may be displayed on output unit 1214 of an obstetrics patient station of the type shown in FIG. 2 in accordance with a non-limiting example of implementation. As depicted, the GUI 1300 includes a display area 1304 conveying pregnancy progression information associated with the obstetrics patient. In this case the display area 1304 conveys a fetal heart rate tracing and a TOCO tracing. The GUI 1300 may also include a user operable control 1302 to allow a user to issue a consultation request over the data network 140 using user input device 1250, which in this case is embodied as a touch sensitive surface on the display. It is to be appreciated that the GUI 1300 shown in FIG. 4 is presented solely for the purpose of illustration and that many alternative implementations are possible.

The apparatus 1200 includes a processor 1206 that may be programmed to process the fetal heart rate signal and the uterine activity signal to derive information related to fetal well-being and/or to process information received over the data network 140 and originating from devices external to the obstetrics patient station $250_a$. The processor 1206 may also be programmed to release a signal for causing output unit 1214 to display the information related to fetal well-being to assist clinicians.

In accordance with a specific implementation, as will be described later below, using a data communication module 1230, the processor may be programmed to establish a communication with the clinical monitoring module 150 (shown in FIG. 1) over the data network 140 in order to communicate data conveying pregnancy progression information associated with the obstetrics patient obtained at the obstetrics patient station $250_a$. It is to be appreciated that the nature of the data sent over the network may vary between implementations. For example, the data sent may include an unaltered version of the signals obtained by the various sensors (e.g. 1210 1211) and/or information received through the user input device 1250 of the obstetrics patient station $250_a$. Alternatively, or in addition, the data sent may include data derived by processing the signals obtained by the various sensors and/or the information received through the user input device 1250 using the processor 1206 according to various methods in order to derive information pertaining to pregnancy progression including fetal and/or maternal well-being.

Clinical Monitoring Module 150

Figure 3:
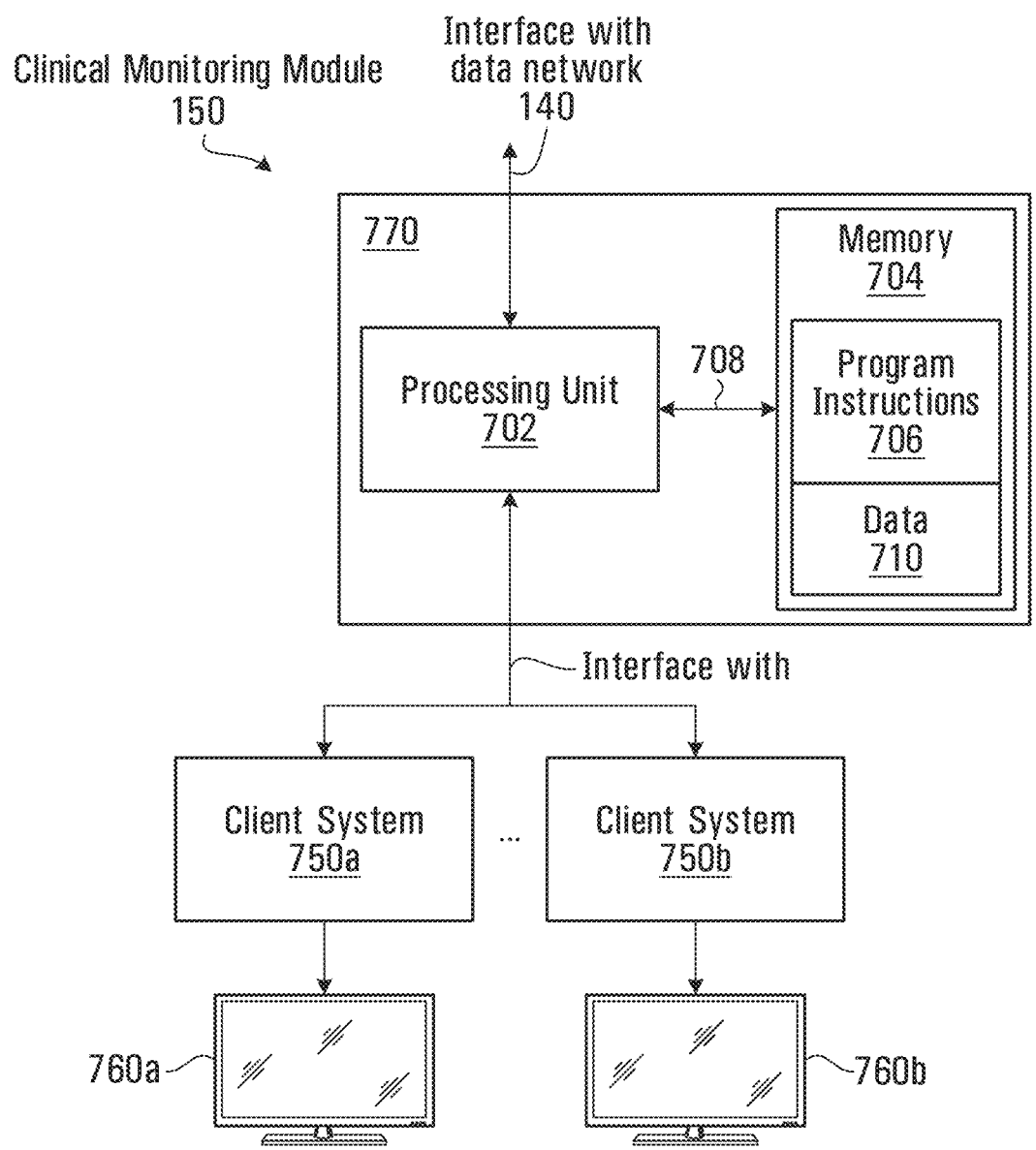
FIG. 3 is a block diagram of the clinical monitoring module 150 of FIG. 1 in accordance with a non-limiting example of implementation.

With reference to FIG. 3, there is shown an example of a configuration of the clinical monitoring module 150 of the system 100 depicted in FIG. 1. It is to be appreciated that the clinical monitoring module 150 may be otherwise configured in alternative implementations and may include more and/or fewer components and therefore this description should be considered as illustrating one amongst different possible implementations.

The clinical monitoring module 150 may be located at, or be in communication with, a virtual center of expertise that would be in communication with one or more remote sites of obstetrics care. In specific implementations, the clinical monitoring module 150 may allow a user to remotely monitor pregnancy progression information associated with a plurality of particular obstetrics patients located in one or more sites of care over data network 140.

As depicted, the clinical monitoring module 150 includes a computing system 770, which in some implementations may be embodied as a computer server, in communication with one or more clinical user stations 750a 750b, which in some implementations may be embodied as client systems.

As shown, the computing system 770 may comprise processing unit 702 and a memory 704 connected by a communication bus 708. The memory 704 includes data 710 and program instructions 706. The processing unit 702 is adapted to process the data 710 and the program instructions 706 in order to implement some of the functional blocks described in this document and depicted in the drawings. For example, the program instructions 706 when executed by the processing unit 702 may implement one or more of the processes that will be described later on in this document with reference to any one of FIGS. 5, 9A and 9B.

Optionally, the data 710 stored in memory 704 may convey information associated with the set of obstetrics patients currently being monitored by the clinical monitoring module 150. Such information may include patient identification information (e.g. name, age, weight), site of care information (e.g. name of site of care, address, phone, local medical expert contact information (e.g. name, phone number, e-mail address etc. . . . )) and/or clinical care information (e.g. contact information of medical expert (e.g. name, phone number, e-mail address etc. . . . )). It is to be appreciated that the type of information stored may vary from one implementation to the other and that the type of information presented above was intended for the purpose of illustration only.

In accordance with some specific implementations, the processing unit 702 may be programmed to establish communication over the data network 140 with one or more of the obstetrics patient station $250_{a \ldots h}$ of the system 100 (shown in FIG. 1) in order to receive data conveying pregnancy progression information associated with obstetrics patient being monitored at the one or more of the obstetrics patient station $250_{a \ldots h}$. The type of data conveying pregnancy progression information received by the processing unit 702 may vary between different practical implementations. Specific practical examples will be further described later in this document.

The processing unit 702 may also be programmed to establish communications over the data network 140 with one or more of the computing devices $160_{a,b}$ (shown in FIG. 1) to transmit and/or receive information to/from the computing devices $160_{a,b}$. For example, the processing unit 702 may communicate with the computing device 160a to transmit data conveying pregnancy progression information associated with the obstetrics patient obtained at the obstetrics patient station $250_a$. It is to be appreciated that the nature of the data sent over the network may vary between implementations. For example, the data sent may include data derived by processing the signals obtained by the various sensors at the patient station $250_a$. Alternatively, or in addition, the data sent may include an electronic notification data associated with a particular obstetrics patient, as will be further described later in this document. The processing unit 702 may also communicate with the computing device $160_a$ in order to receive information conveying data and/or commands, for example information conveying a request for further pregnancy progression information associated with the particular obstetrics patient.

The processing unit 702 may further be programmed to establish communication through one or more interfaces with the clinical user stations $750_a$ $750_b$. For sake of conciseness, and unless indicated otherwise, in the rest of this document, reference will be made to a single clinical user stations $750_a$. However, it will be appreciated that in various implementations, the clinical module 150 may include one or more clinical user stations $750_{a \ldots b}$.

In some practical implementations, the clinical user station $750_a$ may include an output module $760_a$ comprised of a display screen, a printer and/or any other suitable device for conveying pregnancy progression information to a user associated with the clinical user station $760_a$. In a non-limiting implementation, the output module $760_a$ may include a computer screen associated with a computer workstation, the display screen of a computer tablet or the display screen of smart-phone to display a graphical user interface (GUI) conveying information provided by the processing unit 702 in a visual format. The clinical user station $750_a$ may also include one or more user operable control components (not shown in FIG. 3) for allowing a user of the clinical user station $750_a$ to provide commands and/or make selections at the clinical user station $750_a$ to cause the graphical user interface (GUI) to be adapted to display modified information and/or to allow the user of the clinical user station $750_a$ to trigger communications with a medical expert at one of computing devices $160_{a,b}$ (shown in FIG. 1) and/or establish a communication with a computing device located in proximity to a particular obstetrics patient. The one or more user operable control components may be operated by a user at the clinical user station $750_a$ via any suitable user input device, which may include any one or a combination of the following: keyboard, pointing device, touch sensitive surface, actuator/selection switches or speech recognition unit.

Computing Devices $160_{a,b}$ Associated with Medical Experts

In accordance with some specific practical implementations, the computing devices $160_{a,b}$ may be associated with respective medical experts located remotely or in proximity to the obstetrics patients being monitored at sites of care. Optionally, one or more of the computing devices $160_{a,b}$ may be associated with a member of the clinical staff located near the obstetrics patient, for example in the same hospital and/or by a patient's bedside. Optionally, one or more of the computing devices $160_{a,b}$ may be in proximity to a patient and may be comprised of a telepresence robot configured to move within an obstetrics ward and/or a portable computer and or tablet located by a patient's bedside.

In certain embodiments, the computing devices $160_{a,b}$ can each be directly connected to the data network 140 via any suitable hardware/software components, or can be connected with each other via a private network (e.g. a Local Area Network (LAN)), which in turn, can be connected to the data network 140 (e.g. which may be a Wide Area Network (WAN) and/or a public network such as the Internet). The communication link between the computing devices $160_{a,b}$ and the data network 14 can be metallic conductors, optical fibers or wireless.

In specific practical implementations, at least some of the computing devices $160_{a,b}$ may be embodied as smartphones, tablets and/or networked general purpose computers programmed for implementing at least some features described in the present document. The specific nature of the hardware/software used to establish a communication between the computing devices $160_{a,b}$ and the data network 140 may vary between implementations and is not critical to the present invention and will therefore not be described in further detail here.

With reference to FIG. 4, there is shown an example of a configuration of one (1) of the computing devices $160_{a,b}$ of the system 100 depicted in FIG. 1, namely computing device $160_a$. It is to be appreciated that the other computing devices $160_b$ of the system 100 may have similar of different configurations and may implement similar or different functions from those described herein below with reference to obstetrics computing devices $160_a$ and therefore this description should be considered as illustrating one amongst different possible implementations.

As depicted, the computing device $160_a$ includes a processing unit 732 and a memory 734 connected by a communication bus 738. The memory 734 includes data 740 and program instructions 736. The processing unit 732 is adapted to process the data 740 and the program instructions 736 in order to implement some of the features described in the specification and/or depicted in the drawings. In a non-limiting example, the program instructions 736 may be configured to cause the display of GUIs of the type depicted in FIG. 7 and/or FIG. 8.

In accordance with a specific implementation, the processing unit 732 may be programmed to establish a communication over the data network 140 with the clinical monitoring module 150. For example, the processing unit 732 can receive electronic notification data conveying pregnancy progression information associated with at least one particular obstetrics patient associated with a particular one of the obstetrics patient station $250_{a \ldots h}$, as will be further described later in this document. It will be appreciated that the nature of the data received over the network may vary between implementations.

The processing unit 732 may also be programmed to transmit data over the data network 140 to the clinical monitoring module 150 to request further pregnancy progression information associated with the particular obstetrics patient.

As depicted, the processing unit 732 may also include an interface 744 for receiving a control signal and/or user input information from the user of the device 160a, such as but without being limited to a request by the user for additional information associated with at least the particular obstetrics patient, or a request to establish a communication with a specific obstetrics patient station as will be further described later in this document.

The Processes and Functionality that May be Provided by the System 100

Figure 5A:
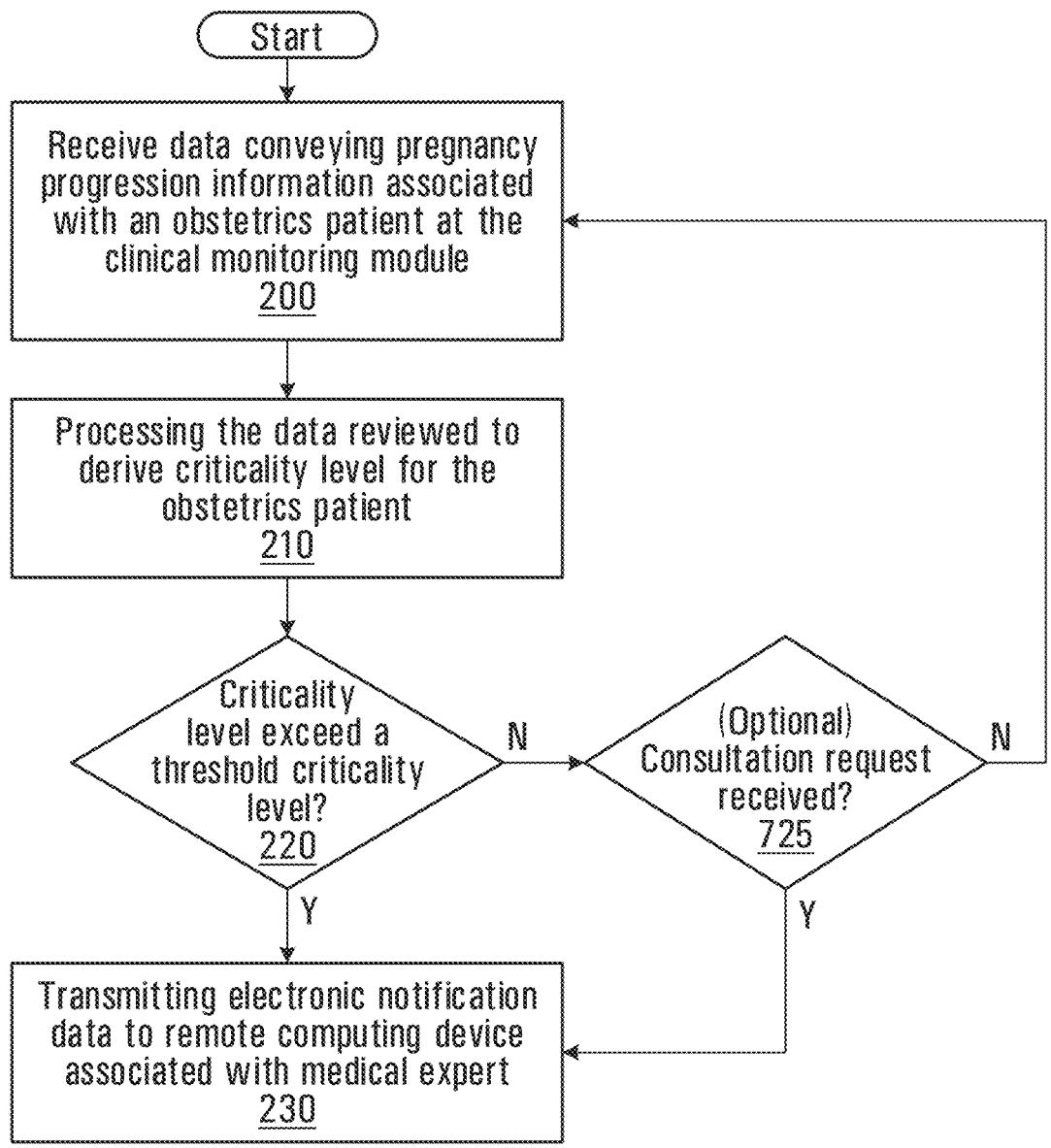
FIGS. 5A and 5B are flow diagrams of a first process that may be implemented by the clinical monitoring module 150 of FIG. 1 for concurrently monitoring of a set of obstetrics patients over a data network in accordance with a non-limiting example of implementation.
Figure 5B:
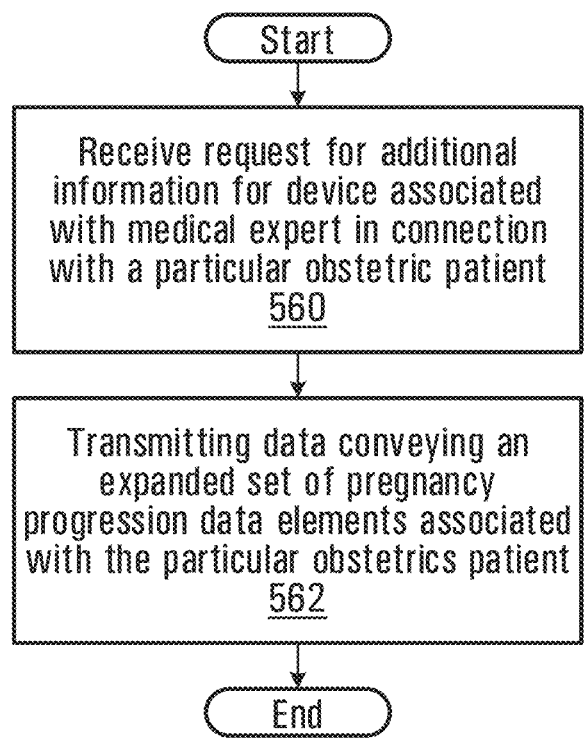

A first embodiment of a process for concurrently monitoring a set of obstetrics patients over a data network that may be implemented by the system 100 will now be described with reference to the flow diagram depicted in FIGS. 5A and 5B. FIGS. 5A and 5B show steps performed from the perspective of the clinical monitoring module 150.

Generally, the process shown in FIG. 5A provides for selectively transmitting electronic notifications in connection with particular obstetrics patients being monitored over the data network 140 from the clinical monitoring module 150 to a particular device 160a or 160b associated with a particular medical expert.

As shown in FIG. 5A, at step 200, data conveying pregnancy progression information associated with respective obstetrics patients in the set of obstetrics patients being monitored is received at the clinical monitoring module 150 over data network 140. With reference to the system depicted in FIG. 1, the data originates from the patient stations $250_{a \ldots h}$ which are interconnected with the clinical monitoring module 150 over the data network 140. As discussed above, the nature of the pregnancy progression data received may vary between different practical implementations but would typically include at least maternal physiological information and fetal vital sign information associated with the respective obstetrics patients in the set of obstetrics patients being monitored.

At step 210, the clinical monitoring module 150 processes the data received at step 200, including the maternal physiological information and fetal vital sign information, to derive information conveying respective criticality levels for the obstetrics patients in the set of obstetrics patients being monitored. The respective criticality levels for the obstetrics patients in the set of obstetrics patients being monitored can be expressed in any suitable manner such as for example a score, a risk levels selected from a set of risk levels, a likelihood, as a percentile value or in any other format suitable for conveying a level of risk associated with the labour. The specific criteria and approach for deriving criticality levels may vary between practical implementations.

In practical implementations, the level of criticality may be based on different dimensions which may include one or more of:

Maternal vital signs
Labour progression indicators (e.g. effacement, cervix dilatation)
Medication
Other maternal physiological information (e.g. uterine contraction information, maternal weight, maternal height, other)
Fetal heart rate (FHR)
(Optional) where a request for a patient consultation was issued In specific non-limiting implementations, the respective criticality levels may be derived using methods described of the type described in one or more of U.S. Pat. No. 6,907,284; and/or U.S. Published Patent Application No. 2007/0255588; and/or U.S. Published Patent Application No. 2008/0039744 and/or U.S. Published Patent Application No. 2010/0268124 and/or U.S. Pat. No. 6,423,016 and/or U.S. Pat. No. 7,959,565. The contents of each of the above noted documents are incorporated herein by reference. It will be appreciated that the specific criteria and rules for setting levels of criticality may vary and may be dependent on hospital policies and/or recognized best practices in the area of obstetrics. The conditions to be met ("the protocol) to assign levels of criticality to specific patients may be specified by the user/owner/operator of the system (or by the organisation/hospital). It will also be appreciated that the set of criteria for deriving criticality levels for the obstetrics patients may be customizable and may evolve over time, adjusting to evolving policies or scientific advances in obstetrics medicine. The specific manner in which a level of criticality of an obstetrics patient is derived is not critical to the invention and will therefore not be described in further detail here.

At step 220, the clinical monitoring module 150 processes the respective criticality levels derived at step 210 to determine whether a notification should be transmitted to a particular device 160a or 160b associated with a particular medical expert. In a specific implementation, such a determination may be made by performing a comparison between the derived criticality levels and a threshold criticality level. The threshold criticality can be established by a user/owner/operator of the system 100 (or by the organisation/hospital) using, e.g., a suitable tool for allowing a user to program the threshold criticality level and/or may be set to a pre-determined value at the time the system 100 is configured.

If at step 220 it is determined that no notification should be transmitted, the process either proceed to optional step 725 (described below) or, if this step is not present, the process loops back to step 200 where the clinical monitoring module 150 continues to receive data conveying pregnancy progression information associated with respective obstetrics patients in the set of obstetrics patients being monitored. It is to be appreciated that steps 200 210 and 220 are repeatedly performed over time with newly received data conveying pregnancy progression information obtained over time so that the evolution of the criticality levels associated with respective patient are dynamically updated and assessed to determine if and when a notification should be sent.

Alternatively if at step 220 it is determined that a notification should be transmitted, the process proceeds to step 230, which will be described below.

Turning now to (optional) step 725, at this step the clinical monitoring module 150 determines whether a consultation request was received in connection with the particular obstetrics patient. In specific practical implementation, the consultation request may originate from the obstetrics patient station amongst the obstetrics patient stations $250_a$ . . . $_h$ associated with the particular obstetrics patient or from a device located in proximity to the particular obstetrics patient. In a non-limiting example, the consultation request may have been entered by the patient herself and/or by someone located at the patient's bedside using at the user input device 1250 (shown in FIG. 2). With reference to the GUI presented on FIG. 11, the consultation request may have triggered by a user actuating the "request consultation" control 1302 displayed on the GUI 1300.

If at step 725 it is determined that no consultation request was received in connection with a particular obstetrics patient, the process loops back to step 200 where the clinical monitoring module 150 continues to receive data conveying pregnancy progression information.

Alternatively if at step 725 it is determined that a notification should be transmitted since a consultation request was received, the process proceeds to step 230, which will be described below.

Advantageously, the processing of a consultation request originating from a device located in proximity to the particular obstetrics patient may allow local medical personnel to seek medical guidance from a remotely located medical expert with respect to a particular obstetrics patient even if the assessed corresponding criticality level does not exceed a reference threshold.

While the assessment of whether a consultation request was received was depicted in FIG. 5 is shown as being a step distinct from steps 200 210 and 220, it will be appreciated that in some specific alternative implementation, data conveying consultation requests may be transmitted and form part of the pregnancy progression information received at step 200 and the deriving of the criticality level at step 210 may therefore take into account receipt of such request. In such non-limiting implementations, the level of criticality associated with a particular obstetrics patient derived at step 220 may be conditioned at least in part based on the presence of the request for consultation received. For example, the presence of the request for consultation could affect a derived criticality level so as to have it exceed the threshold criticality level at step 220 where it would not have done so in absence of the request for consultation.

Moving now to step 230, at this step the clinical monitoring module 150 transmits electronic notification data over the data network 140 to a particular computing device $160_a$ $160_b$, the electronic notification data being sent being associated with a particular obstetrics patient.

Transmitting such notification data to the computing device $160_a$ may allow drawing the attention of the medical expert associated with the computing device $160_a$ to an obstetrics situation associated with a particular obstetrics patient that may require medical intervention.

In some specific practical implementations, the electronic notification data may be in the form of an e-mail message and/or an SMS message and may be transmitted to a specific one of the computing devices $160_{a\ldots b}$. The specific one of the computing devices $160_{a\ldots b}$ to which the e-mail or SMS may be sent may be determined in a number of different manners. For example, the contact information of the particular medical expert (e.g. e-mail address and/or telephone number) may be extracted from a memory, for example memory 704, of the clinical monitoring module 150. The particular medical expert may be (i) specific to the particular obstetric patient for which a message is being sent, (ii) associated to a plurality of obstetrics patients in some logical manner (for example based on geographic proximity), (iii) selected from a pool of available medical experts using some heuristic rule (for example using a round robin type of allocation or in dependence to the criticality level) and/or (iv) determined using any other suitable approach so that the electronic notification data may be sent to a particular medical expert.

In some practical examples of implementation, the electronic notification data is configured for causing a graphical user interface (GUI) to be displayed on a display screen of the computing device 160a associated with the particular medical expert. Example of features that may be presented on such a GUI will be further described later in this document.

In some alternate specific examples of implementation (not shown in the Figures), rather than transmitting an SMS message or an e-mail, the computing devices $160_{a\ldots b}$ may be executing a computer program configures so that electronic notification data transmitted to a specific one of the computing devices $160_{a\ldots b}$ may cause a pop-up window including a GIU to appear on the display screen of specific one of the computing devices $160_{a\ldots b}$.

It is to be appreciated that while the process depicted in FIG. 5A contemplates the use of a single critical threshold for triggering the transmittal of a notification, it is to be appreciated that alternative embodiments may contemplate the use of multiple critical thresholds each of which may trigger respective notifications, the nature of which may vary according to the threshold. Thus, according to such variants, different threshold criticality levels may be contemplated, where exceeding each threshold may trigger different types of electronic notifications. For example, a first threshold criticality level may trigger the transmittal of electronic notification data conveying a notification of a first type (e.g. low level emergency) and be sent to a first medical expert (e.g. an obstetrics intern). A second threshold criticality level may trigger the transmittal of electronic notification data conveying a notification of a second type (e.g. mid-level level emergency) and be sent to the same first medical expert or to a different/second medical expert (e.g. an obstetrician). A third threshold criticality level may trigger the transmittal of electronic notification data conveying a notification of a third type (e.g. hi-level level emergency) and be sent to the same first medical expert or to the second medical expert or to yet a different/third medical expert a second medical expert (e.g. a specialist in obstetrical complications having more experience in trauma for example and/or a medical expert that may be located in proximity to the particular obstetrics patient).

For example, the notification of the first type may include an electronic notification which causes the GUI to display information regarding the FHR having exceeded a first threshold criticality level with respect to a particular obstetrics patient, and the notification of the second type may include an electronic notification which causes the GUI to display information regarding the physiological response of the particular obstetrics patient to oxytocin administration having exceeded a second threshold criticality level. In another example, the notification of the first type may include an electronic notification which causes the GUI to display information regarding the FHR having exceeded a first threshold criticality level with respect to a particular obstetrics patient, e.g., number of late deceleration, and the notification of the second type may include an electronic notification which causes the GUI to display information regarding the FHR having exceeded a second threshold criticality level, e.g., number of decelerations exceeding 60 seconds in duration and decreasing greater than 60 bpm from the baseline, thus distinct from the first threshold criticality level.

In one non-limiting embodiment, the electronic notification data conveying the notification of the second type is transmitted to the computing device 160a associated with the particular medical expert. In another non-limiting embodiment, the electronic notification data conveying the notification of the second type is transmitted to a computing device 160b associated with a second particular medical expert, which is distinct from the first medical expert. In yet another non-limiting embodiment, the electronic notification data conveying the notification of the second type is transmitted to a computing device (not shown) associated with a clinical staff member located in proximity to the particular obstetrics patient.

While not shown in FIG. 5A, following the transmittal of an electronic notification at step 230, the clinical monitoring module 150 may wait for a signal from the computing device $160_a$ $160_b$ to which the electronic notification was sent confirming that the notification was received. In some implementation, failure to receive a signal confirming that the notification was received with a certain time delay from the computing device $160_a$ $160_b$ to which the notification was sent may cause the clinical monitoring module 150 to send another electronic notification (essentially repeating step 230) to either the same computing device to which the first notification was sent or to another computing device associated with another medical expert. The time delay may have fixed duration and/or may be conditioned based on the level of criticality associated with the obstetrics patient. For example, the higher the criticality level, the shorter the time delay for waiting for a signal confirming that the notification was received may be.

Referring now to the process shown in FIG. 5B, this process provides for transmitting data in connection with particular obstetrics patients being monitored over the data network 140 from the clinical monitoring module 150 to a particular device 160a or 160b associated with a particular medical expert in response to a request received from the particular device 160a or 160b.

As depicted, at step 560, the clinical monitoring module 150 receives a request for additional information from a particular device 160a or 160b associated with a particular medical expert and referring to a particular patient. The clinical monitoring module 150 processes a request, at step 562, generates a reply message conveying an expanded set of labour information elements associated to the particular patient. The reply message is then transmitted over the data network to the particular device 160a or 160b from which the request originated.

FIG. 6

Figure 6:
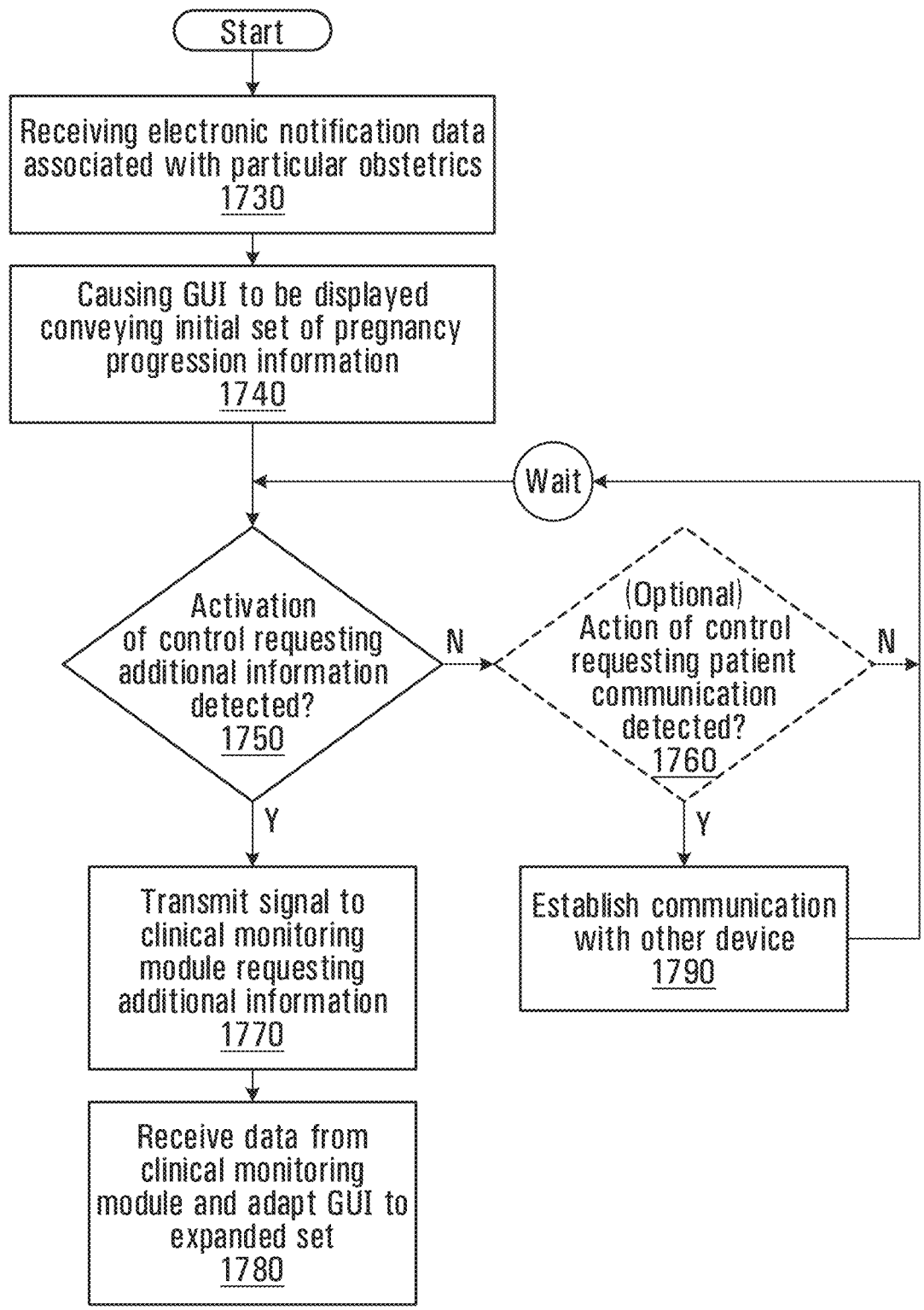
FIG. 6 is a flow diagram of a process that may be implemented by a device used by a medical expert of the type depicted in FIG. 4 in accordance with a non-limiting example of implementation.

An embodiment of a process that may be implemented by the system 100 will now be described with reference to the flow diagram depicted in FIG. 6. FIG. 6 shows steps performed by a computing device associated with a medical expert, such as computing device 160$_a$ or 160$_b$. For this example, we will refer to computing device 160$_a$ simply for the purpose of convenience.

As depicted, at step 1730, computing device 160$_a$ receives over data network 140 electronic notification data associated with a particular obstetrics patient from clinical monitoring module 150, the electronic notification data being configured for causing a graphical user interface (GUI) to be displayed on the display screen of the computing device.

At step 1740, the received the electronic notification data is processed by the processing unit of the computing device 160$_a$ and a GUI is caused to be displayed on the display screen of the computing device 160$_a$. The GUI includes information element conveying pregnancy progression information elements associated with the particular obstetrics patient. It will be readily appreciated that the information conveyed by the GUI may vary significantly between implementations.

Figure 7:
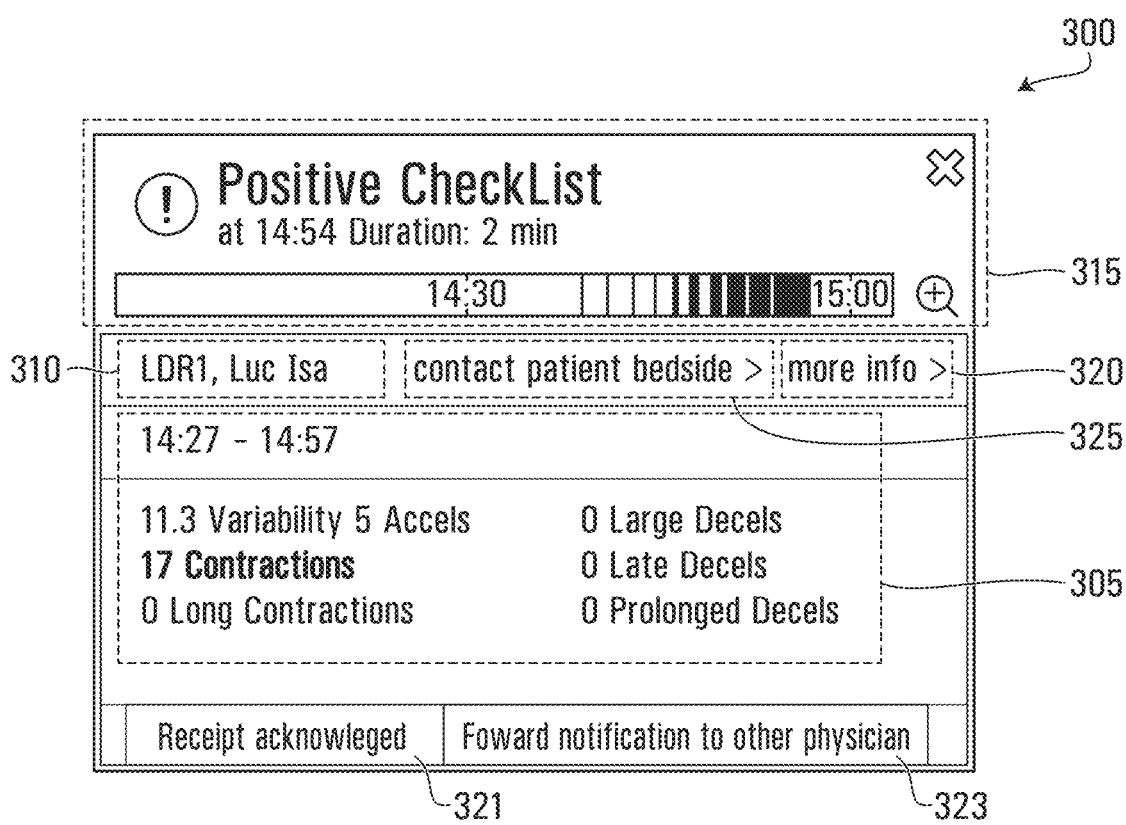
FIG. 7 shows a specific example of implementation of a graphical user interface (GUI) conveying an initial set of pregnancy progression information elements associated with a particular obstetrics patient that may be caused to be displayed on a device of the type depicted in FIG. 4 in accordance with a non-limiting example of implementation.

A non-limiting example of a specific GUI that may be caused to be displayed on the display screen of the computing device 160$_a$ is shown FIG. 7. In a specific implementation, the pregnancy progression information elements displayed on the GUI may form an initial set of pregnancy progression information elements associated with the particular obstetrics patient. This initial set of information displayed on the GUI may be useful in attracting a user's attention to certain aspects of the labour progress of the particular obstetric patient so that the medical expert may get a snap shot of the situation. By displaying an initial set of pregnancy progression information element associated with the particular obstetrics patient, the medical expert may monitor and analyse the pregnancy progression of the respective obstetrics patient based on a more focused, concise and informative information displayed on the graphical window 300.

Optionally, and as depicted, the GUI 300 includes user operable control component 321 to enable the user to issue a message to the clinical monitoring module 150 confirming that the electronic notification has been received and is being looked. In the specific embodiment depicted, the operable control component 321 is provided in the form of touch sensitive areas on the display however it will be appreciated that any suitable format of user operable control may be provided in alternate implementations.

As depicted, the GUI 300 also includes a set of information sections 305 and 310. Information sections 305 and 310 are in the form of text boxes conveying information such as but without being limited to identification of the respective remote site of care associated with the obstetric patient, an identification of the particular obstetrics patient, labour progression information elements associated with the particular obstetrics patient, and derived criticality level. The graphical window 300 may alternatively, or additionally, include a graphical information section 315, which may visually convey other types of pregnancy progression information elements associated with the particular obstetrics patient. In practical implementations, different types of visual identifier codes may be used including, without being limited to, a color code, changes in font sizes, "blinking" displays or any other manner that may assist a user in visually distinguishing between the different types of pregnancy progression information elements associated with the particular obstetrics patient, for example but without being limited to as to whether a given pregnancy progression information element is transient or not.

It should be understood that the window 300 is only a specific example of a specific visual representation of the type of labour that can be conveyed. It is within the scope of the invention for a visual representation to contain more or less information.

In the specific example of implementation, the graphical window 300 also includes one or more user operable control components 320 325 323 to enable the user to request additional information in connection with the particular obstetrics patient and/or to initiate a communication with another device. In the specific embodiment depicted, three user operable control component 320 and/or 325 and/or 323 are provided in the form of touch sensitive areas on the display however it will be appreciated that any suitable format of user operable control may be provided in alternate implementations. It will also be understood that while the above described specific example of provides user operable control components 320 323 and 325 to enable the user to request for a particular action, the reader will readily understand that there may be one or more user operable control components depending on the particular implementation. In one non-limiting embodiment, the user operable control components 320 and/or 325 and/or 323 can cause the display of a list of actions from which the user may select to request for the particular action (not shown).

At computing device 160$_a$, at step 1750, a determination is made as to whether actuation of the control 320 for requesting additional information is detected and at step 1760 a determination is made as to whether actuation of the control 325 or control 323 for initiating a communication with another device is detected. If actuation of control 320 is detected, the process proceeds to step 1770 and if actuation of control 325 or control 323 is detected, the process proceeds to step 1790.

At step 1770, which is initiated in response to actuation of the user operable control component 320 by the user of the computing device 160$_a$, the computing device 160$_a$ causes a signal conveying a request for additional information in to be transmitted from the computing device 160$_a$ to the clinical monitoring module 150. The signal transmitted conveys the required information to identify the particular patient for which information is being requested. Optionally, the signal may also convey the type of information to be provided. While the computing device 160$_a$ waits for the reply of the clinical monitoring module 150, the process then proceed to step 1780.

At step 1780, data originating from the clinical monitoring module 150 is received at the computing device 160$_a$ over the data network 140. The data received is configured to adapt the GUI displayed on the displayed of the computing device 160$_a$ to present the user with an expanded set of pregnancy progression information elements associated with the particular obstetrics patient.

The adapted GUI includes and expanded set of information element conveying pregnancy progression information associated with the particular obstetrics patient. A non-limiting example of a specific adapted GUI that may be caused to be displayed on the display screen of the computing device 160$_a$ is shown FIG. 8. It will be readily appreciated that the information conveyed by the adapted GUI may vary significantly between implementations and therefore the description presented here should be considered as illustrating one amongst different possible implementations.

Figure 8:
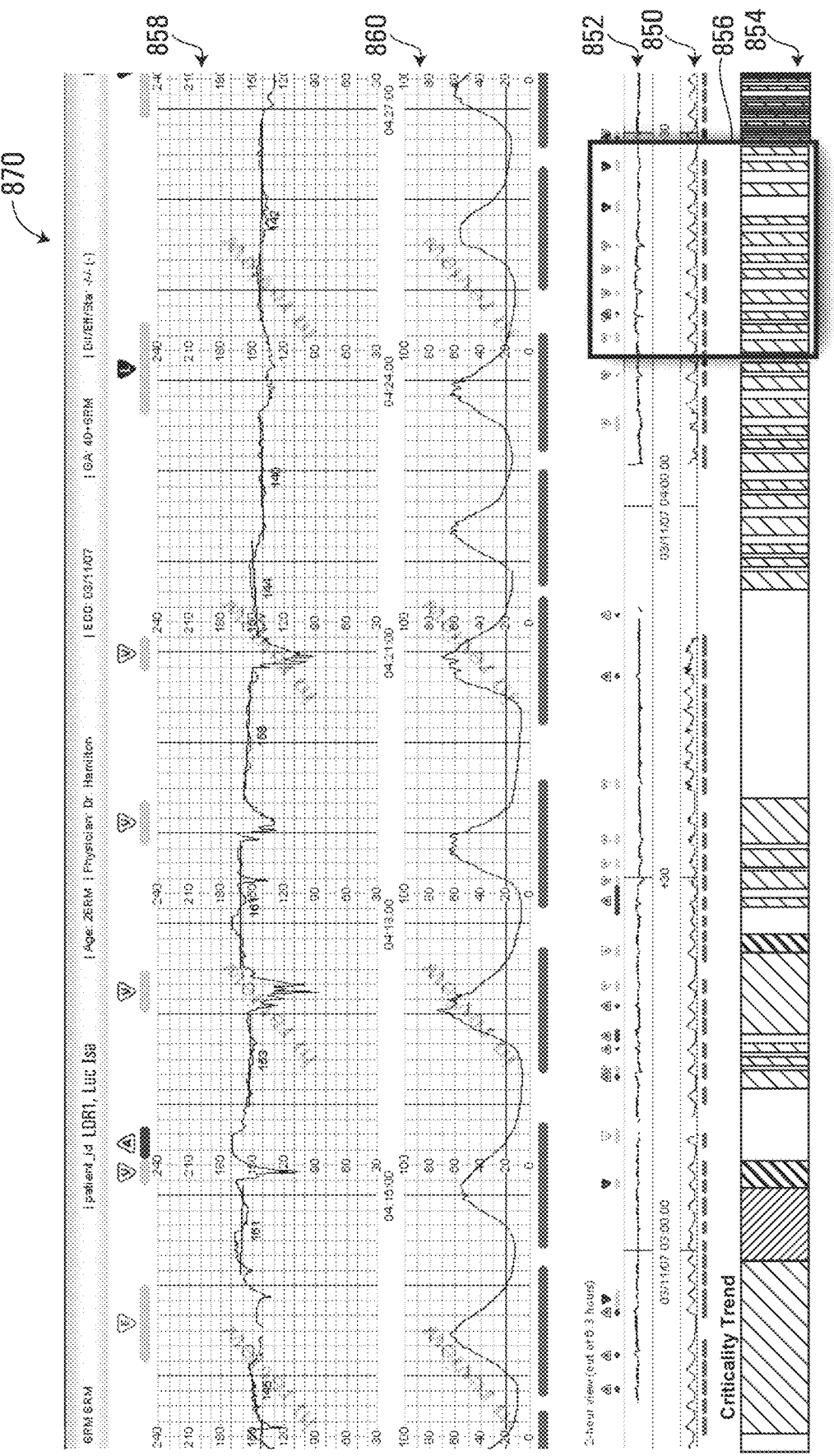
FIG. 8 shows a specific example of implementation of an adapted GUI conveying an expanded set of pregnancy progression information elements associated with a particular obstetrics patient that may be caused to be displayed on the device of the type depicted in FIG. 4 in accordance with a non-limiting example of implementation.

Referring to the particular embodiment shown in FIG. 8, the adapted GUI 870 may include tracings 852 850 conveying a uterine contraction pattern over time (TOCO tracing) and fetal heart rate patterns over time. The tracing 850 conveying a uterine contraction pattern over time is derived on the basis of the contraction signal received from the uterine activity sensor 120 (shown in FIG. 1). The tracing 852 conveying a fetal heart rate pattern over time is derived on the basis of the fetal heart rate signal received from the fetal heart rate sensor 110 (also shown in FIG. 1). As shown the adapted GUI 870 may also include a graph 854 conveying the value of a contractility persistence index over time. In this example a colour scheme is to convey different values of the index over time. In the specific example depicted, the adapted GUI 870 also includes a control in the form of a selection box 856 having a transparent portion superposed on the tracings 850 852 and 854. The portions of the tracings or time signals viewable through the transparent portion correspond to selected portions of the tracings. The selection box 856 is moveable along the time axis (x-axis) such as to allow the user to select a desired time segment.

Below the selection box 856 appears information related to characteristics of the tracings within the transparent portion. More specifically, in the example depicted, an indication of the average number of contraction within the viewing window is presented. When the window is displaced along the x-axis, the information appearing below is accordingly updated to reflect the characteristics of the new portion of the tracings selection by selection box 856.

The adapted GUI 870 depicted includes a tracing 858 conveying a fetal heart rate pattern over time and a tracing 860 conveying a uterine contraction pattern over time (TOCO tracing). The tracing 858 conveying a fetal heart rate pattern over time corresponds to the selected portion of the tracing 852 and is a zoomed-in view of the selected portion of tracing 852 selected by selection box 856.

Considering now to step 1790, which is initiated in response to actuation of the user operable control component 325 or control component 323 by the user of the computing device 160$_a$, the computing device 160$_a$ initiates steps to establish a communication with another device. The other device may be in a location in proximity to the particular obstetrics patient or in another location and may be associated with the particular patient or with another medical expert. For example, the communication established with a computing device associated with the particular obstetrics patient may include one of a telephone call, a video call, an e-mail, an SMS message, an audio alarm trigger and/or a visual alarm trigger. Such communication may allow the medical expert using computing device 160$_a$, who may be remotely located, to interact with the particular obstetrics patient herself and/or with a person at the bedside of the obstetrics patient, which may include a friend/spouse and/or a member of the clinical staff. The type of communication established may vary depending on the particular implementation and/or may be selected by the medical expert through the GUI by providing an input object conveying suitable selectable options on the GUI displayed computing device 160$_a$. For example, the GUI shown in FIG. 7 shows actuation of the control 325 may cause a menu to appear providing different communications options allowing the medical expert to choose amongst communications options of the type mentioned above. Optionally, the types of the selectable options made available through the menu may be dynamically adaptable so as to present the medical expert with options customized to particular circumstances associated with the obstetrics patient. For example, in a case where the electronic notification data was sent to computing device 160$_a$ in part as a result of a consultation request originating from the patient's bedside, the selectable options may include a telephone call and a video call in connection with a device located at the patient's bedside but may exclude an audio alarm trigger and/or a visual alarm trigger to reduce the likelihood the medical expert may trigger alarms unnecessarily. As another example, in a case where the electronic notification data was sent in part as a result of a criticality level exceeding a threshold, the selectable options may include an audio alarm trigger and/or a visual alarm trigger in addition to other options.

Alternatively, rather than enter into communication with someone at the patient's bedside, at step 1790 computing device 160$_a$, may initiate steps to establish a communication with another device associated with another medical expert, which may be in a location in proximity to the particular obstetrics patient (for example the same hospital) or a remote location. The other device may have a configuration similar to that of computing device 160$_a$. The communication established with the computing device associated with the other medical expert may be one of a telephone call, a video call, an e-mail, an SMS message, an audio alarm and a visual alarm trigger.

Alternatively, following actuation of control 323, the communication may be in the form of transmittal of further notification data associated with the particular obstetrics patient over the data network 140. The further electronic notification data may be in the form of an e-mail, an SMS message, an audio alarm trigger and/or a visual alarm trigger. In some specific practical implementations, the further electronic notification data may be in a format similar to the electronic notification data that was sent by the clinical monitoring module 150 and may be configured for causing a graphical user interface (GUI), similar to that displayed on the device 160$_a$, to be displayed on a display screen of the device associated with the other medical expert. In specific practical implementation, the further notification data may convey one or more specific requests for medical care in connection with the particular obstetrics patient. In such implementations, the GUI displayed at the computing device 160$_a$ may provide one or more user operable control components to allow the user to provide specific requests for medical care in connection with the particular obstetrics patient so that such specific requests are included as part of further notification data. Such one or more user operable control components may be in the form of user editable text boxes, menus including a list of selectable medical care options and/or any other suitable mechanism for allowable the user to provide such information through the GUI.

Figure 9A:
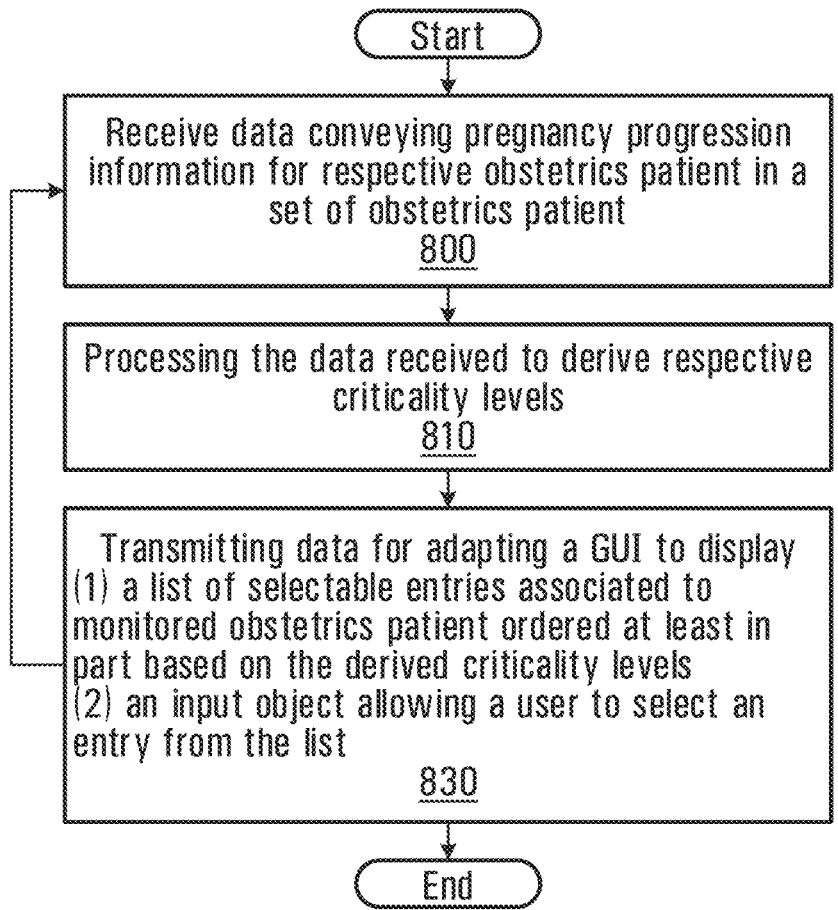
FIGS. 9A and 9B are flow diagrams of a second process that may be implemented by the clinical monitoring module 150 of FIG. 1 for concurrently monitoring of a set of obstetrics patients over a data network in accordance with a non-limiting example of implementation.
Figure 9B:
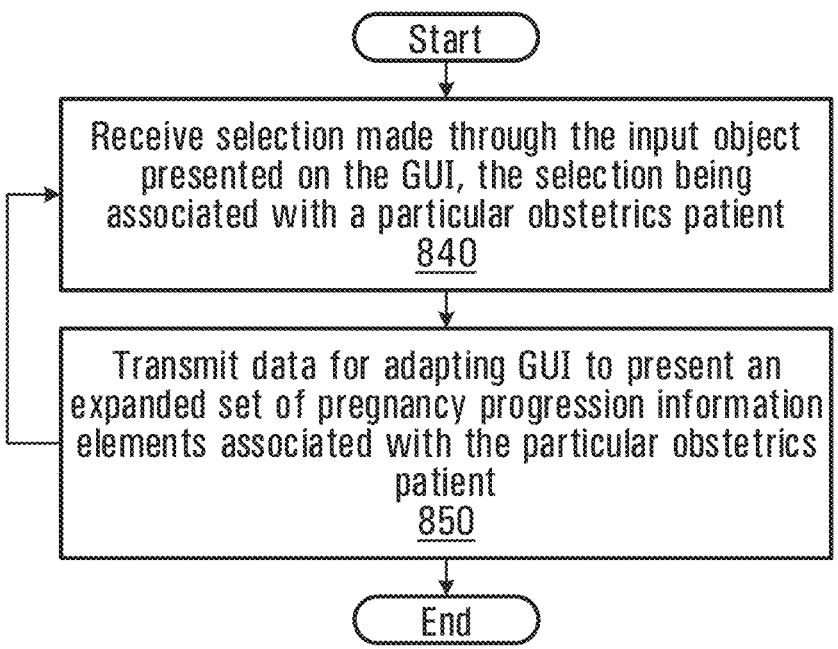

FIGS. 9A and 9B

A first embodiment of a process for concurrently monitoring a set of obstetrics patients over a data network that may be implemented by the system 100 will now be described with reference to the flow diagrams depicted in FIGS. 9A and 9B. FIGS. 9A and 9B show steps that may be performed from the perspective of the clinical monitoring module 150, in addition to or alternatively to the process depicted in FIG. 5.

Generally, the process shown in FIGS. 9A and 9B may allow a user to visualize pregnancy progression information associated with a plurality of obstetrics patients in a manner that facilitates the prioritizations of the patients. In particular, the process suggests presenting GUI including a list of obstetrics patients ordered at least in part based on derived respective criticality levels. It will be apparent that such ordered list may allow the user to more efficiently focus his/her efforts to obstetrics patients presenting a more critical clinical obstetrics situation. The GUI may be dynamically updated over time to adapt the ordered list based on pregnancy progression information newly received at the clinical monitoring module 150.

As shown, at step 800, data conveying pregnancy progression information associated with respective obstetrics patients in the set of obstetrics patients being monitored is received at the clinical monitoring module 150 over data network 140. Step 800 is analogous to step 200 described with reference to FIG. 5 and may be implemented in a similar manner and therefore will not be described in further detail here. The process then proceeds to step 810.

At step 810, the clinical monitoring module 150 processes the data received at step 200, including the maternal physiological information and fetal vital sign information, to derive information conveying respective criticality levels for the obstetrics patients in the set of obstetrics patients being monitored. Step 810 is analogous to step 210 described with reference to FIG. 5 and may be implemented in a similar manner and therefore will not be described in further detail here. The process then proceeds to step 830.

At step 830, the clinical monitoring module 150 processes the respective criticality levels derived at step 810 to cause a graphical user interface displayed on a display device 760a or 706b (shown in FIG. 3) to be adapted to present the user of the clinical user station 750a or 750b with an ordered list including selectable entries associated with one or more obstetrics patients from the set of obstetrics patients being monitored. The selectable entries in the ordered list are arranged in order based on the derived respective criticality levels. The GUI provides an input object configured for accepted a user input specifying a particular obstetrics patient among the one or more obstetrics patients associated with the selectable entries presented to the user.

Figure 10:
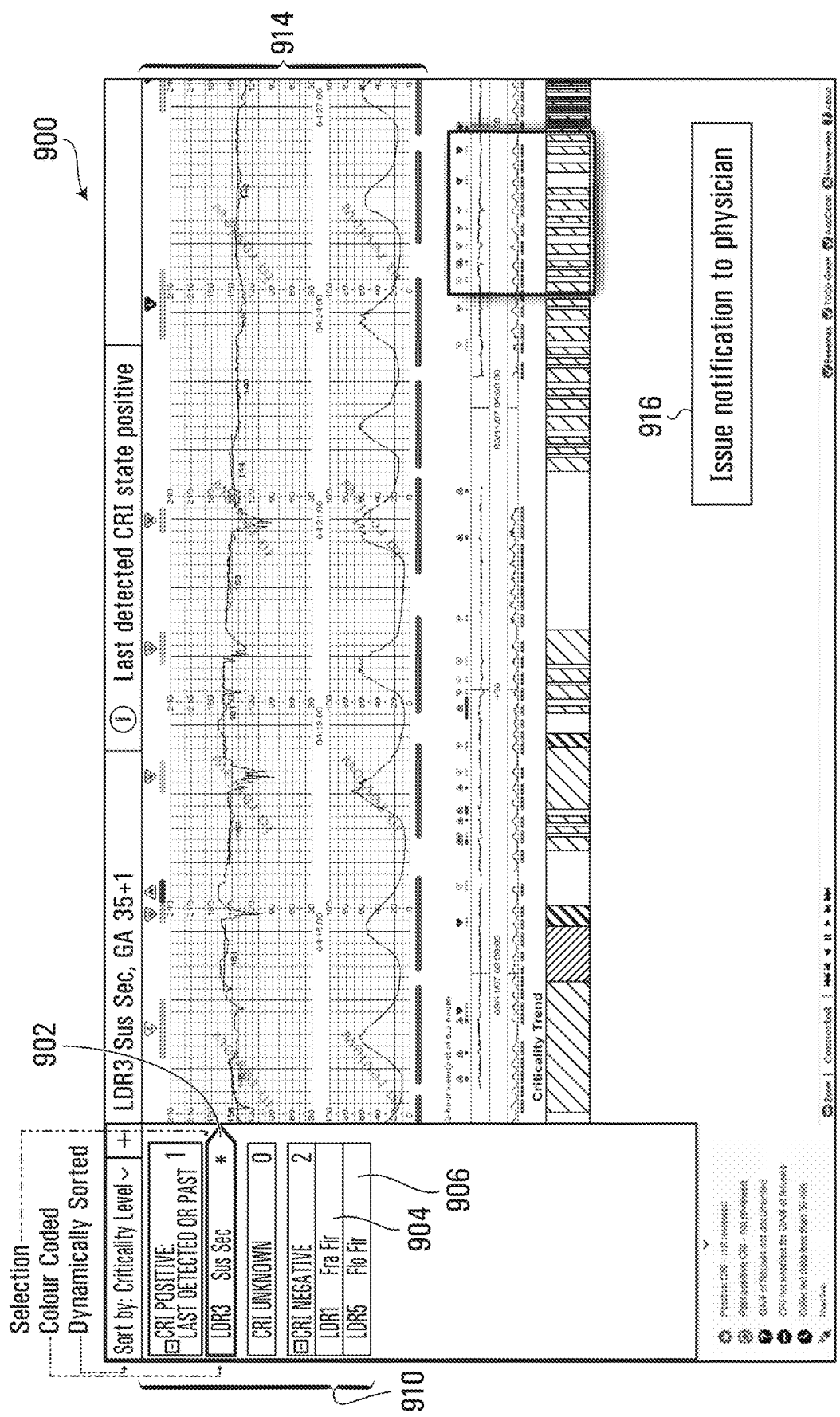
FIG. 10 shows a specific example of implementation of a GUI presenting a user with an ordered list including selectable entries associated with one or more obstetrics patients being monitored, wherein the GUI may be caused to be displayed on a display device by the clinical monitoring module 150 of the type shown in FIGS. 1 and 3 in accordance with a non-limiting example of implementation.

A non-limiting example of a specific GUI that may be caused to be displayed on the display screen 760a of the clinical user station 750a (shown in FIG. 3) is shown FIG. 10. The specific GUI illustrated in FIG. 10 may be caused to be adapted in response to the transmission of data for displaying the ordered list. Accordingly, the GUI of FIG. 10 may be useful in displaying information for allowing the user to more efficiently focus his/her efforts to obstetrics patients in more critical clinical situation.

A depicted, the specific GUI shown in FIG. 10 is in the form of a graphical window 900 that could be shown on the display 760a associated with the clinical user station 750a of the clinical module 150 (shown in FIG. 3). The graphical window 900 may include an information section which includes the ordered list 910 of selectable entries 902, 904 and 906 associated with respective ones of the one or more obstetrics patients from the set of obstetrics patients being monitored by the system 100. The selectable entries in the ordered list 910 are arranged based on the derived respective criticality levels. In the specific embodiment shown in FIG. 10, the ordered list is arranged in descending order with respect to the criticality level. As depicted in this non-limiting example, the selectable entries 902, 904 and 906 are classified by processing the respectively criticality levels associated with the obstetrics patients according to three threshold levels of criticality namely "criticality positive" for entry 902, "criticality unknown" (no entries in this classification) and "criticality negative" for entries 904 and 906. It will be readily apparent that the ordered list 910 may include any number of selectable entries. In particular, it is noted that the ordered list include respective entries for each obstetrics patient in the set of obstetrics patients being monitored or, alternatively, may include respective entries for only a subset of the obstetrics patients in the set of obstetrics patients being monitored.

In some specific practical implementations, the GUI may be configured to assign visual identifiers to the selectable entries in the ordered list 910 in accordance with visual identifier code, by processing respective specific criticality levels derived in connection with the obstetrics patients. In practical implementations, different types of visual identifier codes may be used including, without being limited to, a color code, changes in font sizes, "blinking" displays or any other manner that may assist a user in visually distinguishing between the selectable entries in the ordered list. In a non-limiting implementation, the visual identifier may be in the form of a color code so that the ordered list 910 displayed is color coded so that a user can more readily ascertain which obstetrics patients amongst a group of obstetrics patients are in a critical condition. For example, the graphical window 900 can be configured to display the selectable entries in the ordered list in a particular color in connection with a color code based on the derived respective criticality levels exceeding a threshold criticality level. Advantageously, such arrangement may allow the user to more easily assess the relative criticality level for a particular obstetrics patient in the set of obstetrics patients being monitored. In the embodiment depicted in FIG. 10, entry 902 which is in the "criticality positive" level is shown in a different color than the other entries 904 and 906 to draw the user's attention.

In specific implementations, the GUI 900 is caused to be dynamically adapted over time to present the user with adapted versions of the ordered list adjusted over time, the adjusted versions of the ordered list being derived at least in part by processing the criticality levels for the obstetrics patients adjusted over time.

FIG. 12 shows another specific example of implementation of a GUI presenting a user with an ordered list 910', analogous to the ordered list 910 of FIG. 10, including selectable entries associated with one or more obstetrics patients being monitored in accordance with another non-limiting example of implementation. In this example, only patients associate with a "positive criticality" level are displayed on the GUI. Moving now to FIG. 9B, which may in some cases be performed in parallel with the steps depicted in FIG. 9A, at step 840, user information is received at the clinical monitoring module 150 conveying a selection made by the user of an entry in the ordered list corresponding to a particular obstetrics patient.

At step 850, the user information is processed by the processing unit 702 of the clinical monitoring module 150 and data is transmitted to clinical user stations 750a to adapt the GUI displayed on display device 760a to present the user with an expanded set of pregnancy progression information element associated with the particular obstetrics patient.

With reference to the GUI depicted in FIG. 10, the ordered list 910 configured to accept a user input specifying a particular obstetrics patient among the one or more obstetrics patients associated with the selectable entries presented to the user. In the example depicted, entry 902 is shown as being selected. In response to such selection, the GUI is adapted to present the user with an expanded set of pregnancy progression information 914 associated with the selected particular obstetrics patient, in the same, or in a separate window. In the example depicted, the expanded set of pregnancy progression information may include, for example, but without being limited to detailed tracings/measurements associated with corresponding particular obstetrics patient. It is to be appreciated that the specific information displayed may vary between implementations as is not critical. In the GUI depicted in FIG. 10, the expanded set of pregnancy progression information 914 associated with the selected patient 902 are displayed jointly with the ordered list 910. Advantageously, this may allow the user to visually examine expanded information pertaining to a particular patient while maintaining an overview of the overall set of obstetrics patients being monitored and their relative levels of criticality through the ordered list.

With reference to FIG. 12, user operable controls 1902 1904, displayed in the form of hyperlinks in the specific example shown, are provided to allow a user to select individual entries in the ordered list 910' in order to obtain more detailed information having regard to specific obstetrics patients. Such information may be displayed in a separate window (not shown) that may overlay either partially or completely the GUI depicted in FIG. 12, It will be appreciated that these steps (steps 840 and 850) represent a possible iterative process thus allowing the user to obtain an expanded set of pregnancy progression information associated with more than one particular obstetrics patient from the ordered list. The iterative nature of these operations is illustrated in FIG. 9B with the arrow going from step 850 to step 840.

Looking again to the GUI 900 depicted in FIG. 10, the GUI 900 may provide the user with a user operable control component 916 to enable the user to cause electronic notification data to be transmitted over the data network 140 in connection with the particular obstetrics patient to a computing device (e.g. 160$_a$ or 160$_b$ shown in FIG. 1) associated with a particular medical expert. In the embodiment depicted, the user operable control component 916 is in the form of an area on the GUI 900 which may be actuated using any suitable input device such as a keyboard, pointing device, touch sensitive surface, actuator/selection switches, speech recognition unit and the like. In specific practical implementations, the electronic notification data may be in a form similar to that described earlier with reference to step 230 shown in FIG. 5 and may be configured for causing a graphical user interface (GUI), analogous to GUI 300 depicted in FIG. 7, to be displayed on a display screen of the computing device associated with the particular medical expert, the GUI including pregnancy progression information elements associated with the particular obstetrics patient.

In yet another specific example of implementation, operations performed at the programmable system 100 may comprise any combination of the embodiments described previously. For example, the operations performed at the clinical monitoring module 150 may comprise a combination of the process depicted in FIG. 5 and the process depicted in FIGS. 9A and 9B. It will be appreciated that such specific implementation allows a user to obtain an ordered list of obstetrics patients at least based on respective criticality levels as well as to receive an electronic notification at least partly based on a computed criticality level associated with a particular obstetrics patient. In other words, while the system provides the user at the clinical monitoring module 150 with an ordered list of obstetrics patients at least based on respective criticality levels allowing the user to focus his/her efforts to obstetrics patients in more critical clinical situation, the system can also alert a remotely located medical expert by way of an electronic notification data being transmitted to a computing device associated with the medical expert.

Data Conveying Pregnancy Progression Information

The data conveying pregnancy progression information, which is received at the clinical monitoring module 150 includes at least maternal physiological information and fetal vital sign information associated with respective obstetrics patients in the set of obstetrics patients being monitored.

In specific implementations, the pregnancy progression information associated with the respective obstetrics patients may include maternal vital signs (e.g. maternal heart rate, oxygen saturation etc. . . . ), labour progression indicators (e.g., effacement, cervix dilatation, etc.), medication (e.g., pain medication, epidural status, labour induction with, e.g., oxytocin, anti-viral medicine administration, etc.), other maternal physiological information (e.g. uterine contraction information, maternal weight, maternal height, etc. . . . ), fetal vital sign information such as fetal heart rate (FHR) information and the like.

In a specific example of implementation, the pregnancy progression information associated with respective obstetrics patients in the set of obstetrics patients being monitored includes fetal vital sign information, which may be derived from a labour tool such as described in U.S. Pat. No. 6,907,284, entitled "Method and apparatus for displaying a heart rate signal", which issued Jun. 14, 2005. The content of the above noted document is incorporated herein by reference.

In a specific example of implementation, the pregnancy progression information associated with respective obstetrics patients in the set of obstetrics patients being monitored includes labour progression indicators, which may be derived from labour tools such as described in U.S. Published Patent Application No. 2007/0255588, entitled "Method and apparatus for displaying labour related information associated to an obstetrics patient", U.S. Published Patent Application No. 2008/0039744, entitled "Method and apparatus for providing contraction information during labor progression" and U.S. Published Patent Application No. 2010/0268124, entitled "Method and apparatus for providing contraction information during labor". The content of each of the above noted document is incorporated herein by reference.

In a specific example of implementation, the pregnancy progression information associated with respective obstetrics patients in the set of obstetrics patients being monitored may be derived from labour tools such as described in U.S. Pat. No. 6,423,016, entitled "System and method for evaluating labor progress during childbirth", which issued Jul. 23, 2002. The content of the above noted document is incorporated herein by reference.

In a specific example of implementation, the pregnancy progression information associated with respective obstetrics patients in the set of obstetrics patients being monitored may be derived using any suitable tools such as those of the type described in U.S. Pat. No. 7,959,565, entitled "Method and system for estimating a likelihood of shoulder dystocia", which issued Jun. 14, 2011. The content of the above noted document is incorporated herein by reference.

It will be readily apparent that additional tools may be included in, and certain tools omitted from, the clinical monitoring module 150 without detracting from the invention. It will also be apparent that, while the embodiment contemplates that the tools be implementation by the clinical monitoring module 150, in alternative embodiments certain tools may be implemented by the obstetrics patient station 250a (shown in FIG. 2), while other tools may be implemented by the computing device 160a (shown in FIG. 4), and other tools may be implemented in the clinical monitoring module 150 (shown in FIG. 3). The reader will also appreciate that a tool may be partly implemented in various elements of the system 100, such that a combination of elements would be required to implement the complete tool and derive the pregnancy progression information associated with respective obstetrics patients in the set of obstetrics patients being monitored.

Optionally, the data which is received at the clinical monitoring module 150 may also convey other types of physiological information associated with respective obstetrics patients in the set of obstetrics patients being monitored. For example, such physiological information may include maternal weight, maternal height, estimated fetal weight, maternal diabetes status, and the like. Such physiological information associated with respective obstetrics patients in the set of obstetrics patients being monitored may be obtained via retrieval from a database and/or may be entered by a user through a user interface associated with the one or more computing devices interconnected with the programmable system 100.

Specific Physical Implementation

Those skilled in the art should appreciate that in some embodiments of the invention, all or part of the functionality for previously described herein with reference to the obstetrics patient stations $250_{a \ldots h}$ (shown in FIG. 2), the clinical monitoring module 150 (shown in FIG. 3) and/or the devices $160_{a \ldots b}$ for use by medical experts (shown in FIG. 4) may be implemented as pre-programmed hardware or firmware elements (e.g., application specific integrated circuits (ASICs), electrically erasable programmable read-only memories (EEPROMs), etc.), or other related components.

In other embodiments of the invention, all or part of the functionality previously described herein may be implemented as computer program products including instructions that, when executed, cause a programmable system including at least one programmable processor to perform operations. In practical implementations, the program product could be stored on a medium which is fixed (non-transitory), tangible and readable directly by the programmable system, (e.g., removable diskette, CD-ROM, ROM, PROM, EPROM, flash memory or fixed disk), or the instructions could be stored remotely but be transmittable to the programmable system via a modem or other interface device (e.g., a communications adapter) connected to a network over a transmission medium. The transmission medium may be either a wired medium (e.g., optical or analog communications lines) or a medium implemented using wireless techniques (e.g., microwave, infrared or other transmission schemes).

Other examples of implementations will become apparent to the reader in view of the teachings of the present description and as such, will not be further described here.

The phrases "connected to" and "in communication with" refer to any form of interaction between two or more entities, including mechanical, electrical, magnetic, and electromagnetic interaction. Two components may be connected to each other even though they are not in direct contact with each other and even though there may be intermediary devices between the two components.

Note that titles or subtitles may be used throughout the present disclosure for convenience of a reader, but in no way these should limit the scope of the invention. Moreover, certain theories may be proposed and disclosed herein; however, in no way they, whether they are right or wrong, should limit the scope of the invention so long as the invention is practiced according to the present disclosure without regard for any particular theory or scheme of action.

All references cited throughout the specification are hereby incorporated by reference in their entirety for all purposes.

It will be understood by those of skill in the art that throughout the present specification, the term "a" used before a term encompasses embodiments containing one or more to what the term refers. It will also be understood by those of skill in the art that throughout the present specification, the term "comprising", which is synonymous with "including," "containing," or "characterized by," is inclusive or open-ended and does not exclude additional, un-recited elements or method steps.

Unless otherwise defined, all technical and scientific terms used herein have the same meaning as commonly understood by one of ordinary skill in the art to which this invention pertains. In the case of conflict, the present document, including definitions will control.

As used in the present disclosure, the terms "around", "about" or "approximately" shall generally mean within the error margin generally accepted in the art. Hence, numerical quantities given herein generally include such error margin such that the terms "around", "about" or "approximately" can be inferred if not expressly stated.

Although the present invention has been described with reference to certain preferred embodiments thereof, variations and refinements are possible and will become apparent to the person skilled in art in light of the present description. Therefore, the scope of the invention should be limited only by the appended claims and their equivalents.

The invention claimed is:

1. A computer program product, comprising one or more tangible non-transitory computer readable storage media storing computer executable instructions, for allowing a user to concurrently monitor a set of obstetrics patients over a data network and for directing user attention towards one or more patients in the set of obstetrics patients, the set of obstetrics patients including two or more obstetrics patients, the computer executable instructions, when executed, cause a programmable system including at least one programmable processor to perform operations, the operations comprising:

a) receiving data over the data network from one or more computing devices interconnected with the programmable system over the data network, the received data conveying pregnancy progression information associated with respective obstetrics patients in the set of obstetrics patients being monitored, the pregnancy progression information including at least maternal physiological information and fetal vital sign information obtained over time and being associated with the respective obstetrics patients in the set of obstetrics patients being monitored;

b) processing the data conveying the pregnancy progression information to adjust over time respective criticality levels for the obstetrics patients in the set of obstetrics patients being monitored, the respective criticality levels being derived at least in part by processing the maternal physiological information and the fetal vital sign information;

c) transmitting data to a computing device associated with the user to adapt a graphical user interface (GUI) displayed on a display screen at the computing device to provide the user with an input object presenting the user with:

i) an ordered list including selectable entries associated with one or more obstetrics patients from the set of obstetrics patients being monitored, the ordered list being derived at least in part by processing the derived respective criticality levels for the obstetrics patients in the set of obstetrics patients being monitored, the selectable entries in said ordered list being arranged in order based on the derived respective criticality levels to draw attention towards patients in the set of obstetrics patients having higher criticality levels than other obstetrics patients in the set of obstetrics patients, wherein the GUI is configured to be dynamically adapted over time in response to changes in the respective criticality levels of the obstetrics patients in the set of obstetrics patients being monitored to present the user with adjusted versions of the ordered list over time;

ii) said input object being configured to accept a user input identifying a specific obstetrics patient among the one or more obstetrics patients associated with the selectable entries presented to the user in the ordered list;

d) receiving from the computing device associated with the user information input by the user conveying a selection by the user of the specific obstetrics patient at the input object;

e) in response to receipt of the information input by the user conveying the selection of the specific obstetrics patient, transmitting data to the computing device associated with the user to adapt the GUI at the computing device to present the user with an expanded set of pregnancy progression information elements associated with the specific obstetrics patient.

2. A computer program product as defined in claim 1, wherein the GUI displayed at the computing device is adapted to present the user with the expanded set of pregnancy progression information elements associated with the specific obstetrics patient jointly with the ordered list including selectable entries associated with one or more obstetrics patients from the set of obstetrics patients being monitored.

3. A computer program product as defined in claim 1, wherein the GUI is configured to assign visual identifiers to the selectable entries in said ordered list in accordance with visual identifier code, a specific visual identifier in the visual identifier code being assigned to a specific entry in the ordered list associated with the specific obstetrics patient at least in part based on a specific criticality level derived in connection with the specific obstetrics patient.

4. A computer program product as defined in claim 3, wherein the visual identifier code includes a color code, said GUI being configured to assign colors to the selectable entries in said ordered list in accordance with the color code, a specific color in the color code being assigned to a specific entry in the ordered list associated with the specific obstetrics patient at least in part based on a specific criticality level derived in connection with the specific obstetrics patient.

5. A computer program product as defined in claim 1, wherein the GUI is configured to display the selectable entries in said ordered list in a specific color in connection with a color code based on the derived respective criticality levels exceeding a threshold criticality level.

6. A computer program product as defined in claim 1, wherein the GUI provides the user with a user operable control component to enable the user to cause electronic notification data to be transmitted over the data network in connection with the specific obstetrics patient specified by the user input, the electronic notification data being transmitted to a computing device associated with a specific medical expert.

7. A computer program product as defined in claim 6, wherein the electronic notification data transmitted to the computing device associated with the specific medical expert is configured for causing a graphical user interface (GUI) to be displayed on a display screen of the computing device associated with the specific medical expert, the GUI including pregnancy progression information elements associated with the specific obstetrics patient.

8. A computer program product as defined in claim 7, wherein the pregnancy progression information elements form an initial set of pregnancy progression information elements associated with the specific obstetrics patient, said GUI providing the medical expert with a user operable control component to enable the user to request additional information associated with the specific obstetrics patient, wherein actuation of the user operable control component by the medical expert causes a signal conveying a request for additional information to be transmitted from the computing device to the programmable system.

9. A computer program product as defined in claim 7, wherein said GUI provides the medical expert with a user operable control component to enable the user to establish a communication with a computing device located in proximity to the specific obstetrics patient.

10. A computer program product as defined in claim 9, wherein the communication established with the computing device associated with the specific obstetrics patient is one of a telephone call, a video call, an e-mail, an SMS message, an audio alarm and a visual alarm trigger.

11. A computer program product as defined in claim 1, wherein the maternal physiological information associated with the respective obstetrics patients in the set of obstetrics patients being monitored includes at least one of maternal vital signs, labour progression indicators and medication.

12. A computer program product as defined in claim 1, wherein the fetal vital sign information associated with the respective obstetrics patients in the set of obstetrics patients being monitored includes fetal heart rate (FHR).

13. A computer program product as defined in claim 1, wherein the user is located in a virtual center of expertise.

14. A method for allowing a user to concurrently monitor a set of obstetrics patients over a data network and for directing user attention towards one or more patients in the set of obstetrics patients, the set of obstetrics patients including two or more obstetrics patients, the method being implemented by a programmable system including at least one programmable processor, said method comprising:

a) receiving data over the data network from one or more computing devices interconnected with the programmable system over the data network, the received data conveying pregnancy progression information associated with respective obstetrics patients in the set of obstetrics patients being monitored, the pregnancy progression information including at least maternal physiological information and fetal vital sign information obtained over time and being associated with the respective obstetrics patients in the set of obstetrics patients being monitored;

b) using the programmable system, processing the data conveying the pregnancy progression information to adjust over time respective criticality levels for the obstetrics patients in the set of obstetrics patients being monitored, the respective criticality levels being derived at least in part by processing the maternal physiological information and the fetal vital sign information;

c) transmitting data to a computing device associated with the user to adapt a graphical user interface (GUI) displayed on a display screen at the computing device to provide the user with an input object presenting the user with:
  i) an ordered list including selectable entries associated with one or more obstetrics patients from the set of obstetrics patients being monitored, the ordered list being derived at least in part by processing the derived respective criticality levels for the obstetrics patients in the set of obstetrics patients being monitored, the selectable entries in said ordered list being arranged in order based on the derived respective criticality levels to draw attention towards patients in the set of obstetrics patients having higher criticality levels than other obstetrics patients in the set of obstetrics patients, wherein the GUI is configured to be dynamically adapted over time in response to changes in the respective criticality levels of the obstetrics patients in the set of obstetrics patients being monitored to present the user with adjusted versions of the ordered list over time;
  ii) said input object being configured to accept a user input identifying a specific obstetrics patient among the one or more obstetrics patients associated with the selectable entries presented to the user in the ordered list;
d) receiving from the computing device associated with the user information input by the user conveying a selection by the user of the specific obstetrics patient at the input object;
e) in response to receipt of the information input by the user conveying the selection of the specific obstetrics patient, processing the selection by the user to derive an expanded set of pregnancy progression information associated with the specific obstetrics patient and transmitting data to the computing device associated with the user to adapt the GUI at the computing device to present the user with the expanded set of pregnancy progression information elements associated with the specific obstetrics patient.

15. A method as defined in claim 14, wherein the GUI displayed at the computing device is adapted to present the user with the expanded set of pregnancy progression information elements associated with the specific obstetrics patient jointly with the ordered list including selectable entries associated with one or more obstetrics patients from the set of obstetrics patients being monitored.

16. A method as defined in claim 14, wherein the GUI is configured to assign visual identifiers to the selectable entries in said ordered list in accordance with visual identifier code, a specific visual identifier in the visual identifier code being assigned to a specific entry in the ordered list associated with the specific obstetrics patient at least in part based on a specific criticality level derived in connection with the specific obstetrics patient.

17. A method as defined in claim 15, wherein the visual identifier code includes a color code.

18. A method as defined in claim 14, wherein the GUI is configured to display the selectable entries in said ordered list in a specific color in connection with a color code based on the derived respective criticality levels exceeding a threshold criticality level.

19. A system suitable for concurrently monitoring a set of obstetrics patients over a data network and for directing user attention towards one or more patients in the set of obstetrics patients, the set of obstetrics patients including two or more obstetrics patients, the system comprising:
  a) one or more devices configured for obtaining pregnancy progression information associated with respective obstetrics patients in the set of obstetrics patients being monitored;
  b) a display device associated with the user;
  c) a clinical monitoring module interconnected with the one or more devices and with said display device, said clinical monitoring module being configured for:
    i) receiving data from the one or more devices, said data conveying the pregnancy progression information associated with the respective obstetrics patients in the set of obstetrics patients being monitored, the pregnancy progression information including at least maternal physiological information and fetal vital sign information obtained over time and being associated with the respective obstetrics patients in the set of obstetrics patients being monitored;
    ii) processing the data conveying the pregnancy progression information to adjust over time respective criticality levels for the obstetrics patients in the set of obstetrics patients being monitored, the respective criticality levels being derived at least in part by processing the maternal physiological information and the fetal vital sign information;
    iii) causing a graphical user interface (GUI) to be displayed on the display device user, the GUI providing the user with an input object presenting the user with:
      (1) an ordered list including selectable entries associated with one or more obstetrics patients from the set of obstetrics patients being monitored, the ordered list being derived at least in part by processing the derived respective criticality levels for the obstetrics patients in the set of obstetrics patients being monitored, the selectable entries in said ordered list being arranged in order based on the derived respective criticality levels to draw attention towards patients in the set of obstetrics patients having higher criticality levels than other obstetrics patients in the set of obstetrics patients, wherein the GUI is configured to be dynamically adapted over time in response to changes in the respective criticality levels of the obstetrics patients in the set of obstetrics patients being monitored to present the user with adjusted versions of the ordered list over time;
      (2) said input object being configured to accept a user input identifying a specific obstetrics patient among the one or more obstetrics patients associated with the selectable entries presented to the user in the ordered list;
    iv) receiving information input by the user conveying a selection by the user of the specific obstetrics patient at the input object;
    v) in response to receipt of the information input by the user conveying the selection of the specific obstetrics patient, processing the selection by the user to derive an expanded set of pregnancy progression information associated with the specific obstetrics patient and adapt the GUI displayed on the display device to present the user with the expanded set of pregnancy progression information elements associated with the specific obstetrics patient.

20. A system as defined in claim 19, wherein the GUI is configured to assign visual identifiers to the selectable entries in said ordered list in accordance with visual identifier code, a specific visual identifier in the visual identifier code being assigned to a specific entry in the ordered list associated with the specific obstetrics patient at least in part based on a specific criticality level derived in connection with the specific obstetrics patient.

21. A system as defined in claim 20, wherein the visual identifier code includes a color code.

22. A system as defined in claim 19, wherein the GUI is configured to display the selectable entries in said ordered list in a specific color in connection with a color code based on the derived respective criticality levels exceeding a threshold criticality level.

* * * * *